United States Patent
Briggs et al.

(10) Patent No.: US 6,187,970 B1
(45) Date of Patent: *Feb. 13, 2001

(54) PROCESSES FOR PRODUCING 1,6-HEXANEDIOLS

(75) Inventors: John Robert Briggs, Charleston; Diane Lee Packett; David Robert Bryant, both of South Charleston; Ailene Gardner Phillips, Charleston; David James Schreck, Cross Lanes; Anil Sakharam Guram, Hurricane; Kurt Damar Olson; Thomas Carl Eisenschmid, both of Cross Lanes; Eric Bruce Tjaden, Charleston, all of WV (US)

(73) Assignee: Union Carbide Chemicals & Plastics Technology Corporation, Danbury, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/843,390

(22) Filed: Apr. 15, 1997

Related U.S. Application Data

(60) Provisional application No. 60/016,287, filed on Apr. 24, 1996, provisional application No. 60/015,952, filed on Apr. 24, 1996, provisional application No. 60/016,179, filed on Apr. 24, 1996, and provisional application No. 60/016,129, filed on Apr. 24, 1996.

(51) Int. Cl.[7] ............................ C07C 31/20; C07C 29/36; C07C 29/17

(52) U.S. Cl. .................... 568/853; 568/852; 568/909; 568/914

(58) Field of Search .......................... 568/853, 852, 568/857, 862, 909, 914, 451, 454, 456

(56) References Cited

U.S. PATENT DOCUMENTS

| | | | |
|---|---|---|---|
| 3,239,566 | 3/1966 | Slaugh et al. | 260/604 |
| 3,660,493 | 5/1972 | Johnson et al. | 260/604 |
| 3,917,661 | * 11/1975 | Pruett . | |
| 3,947,503 | 3/1976 | Kummer | 260/635 |
| 4,214,109 | 7/1980 | Carlock | 568/909 |
| 4,224,255 | 9/1980 | Smith | 568/451 |
| 4,248,802 | * 2/1981 | Kuntz | 568/454 |
| 4,263,449 | 4/1981 | Saito et al. | 560/263 |
| 4,376,212 | 3/1983 | Ohyama et al. | 560/205 |
| 4,447,611 | 5/1984 | Hoshiyama et al. | 586/882 |
| 4,451,679 | 5/1984 | Knifton et al. | 568/909 |
| 4,469,895 | 9/1984 | Knifton et al. | 568/454 |
| 4,536,347 | * 8/1985 | Horner . | |
| 4,612,403 | * 9/1986 | Virnig | 568/454 |
| 4,647,707 | 3/1987 | van Vliet | 568/882 |
| 4,658,068 | 4/1987 | Henin | 568/451 |
| 4,929,776 | * 5/1990 | Grosselin . | |
| 5,177,228 | 1/1993 | Sato et al. | 554/129 |
| 5,235,113 | * 8/1993 | Sato | 568/454 |
| 5,306,848 | 4/1994 | Vargas | 568/883 |
| 5,312,996 | * 5/1994 | Packett | 568/454 |
| 5,504,261 | 4/1996 | Mullin et al. | 568/862 |
| 5,583,250 | 12/1996 | Bahrmann et al. | 560/76 |
| 5,639,920 | * 6/1997 | Yamamoto | 568/862 |
| 5,684,208 | * 11/1997 | Bahrmann | 568/454 |

FOREIGN PATENT DOCUMENTS

| | | |
|---|---|---|
| 0183545 | 6/1986 | (EP) . |
| 0343819 | 11/1989 | (EP) . |
| 0420510 | 3/1991 | (EP) . |
| 0448848 | 10/1991 | (EP) . |
| 0602442 | 6/1994 | (EP) . |
| 0761634 | 3/1997 | (EP) . |
| 1254222 | 11/1971 | (GB) . |
| 1357735 | 6/1974 | (GB) . |
| 1087510 | 4/1984 | (RU) . |
| 150453 | 9/1991 | (RU) . |

OTHER PUBLICATIONS

T904,0421 a defensive publication from the USpatent office, Copelin ser No. 166, 315, 1972.*
CA 80:120229 abs of FR 2180462, Jan. 4, 1974.*
CA:110:57059 abs of paper by Gvinter in Izv Akad Nauk SSSR, (4) pp. 755–759, 1988.*
CA:81:37175 abs of paper by Freudlin in Izv Akad Nauk SSSR, (4) pp. 812–814, 1974.*
CA:72:66276 abs of paper by Vinnits'kii in Neftekhimiya 9(5) pp. 767–770, 1969.*
CA:93:25875 abs of paper by Meng in Huan Ching K'o Hsueh 1 (2) pp. 75–76, 1980.*
CA:103:142435 abs Polymer by Andeis et al 26(7) pp. 1099–1104, 1985.*
J.M. Anderson, et al. *Improved regioselectivity in the hydroformylation reaction catalysed by zeolite–encapsulated rhodium(I) species*, Chem. Commun. 1996, pp. 1543–1544.

(List continued on next page.)

*Primary Examiner*—Gary Geist
*Assistant Examiner*—Jean F Vollano
(74) *Attorney, Agent, or Firm*—Gerald L. Coon

(57) ABSTRACT

This invention relates in part to processes for producing one or more substituted or unsubstituted 1,6-hexanediols which comprise subjecting one or more substituted or unsubstituted penten-1-ols to reductive hydroformylation in the presence of a reductive hydroformylation catalyst, e.g., a metal-organophosphorus ligand complex catalyst, to produce said one or more substituted or unsubstituted 1,6-hexanediols. The substituted and unsubstituted 1,6-hexanediols produced by the processes of this invention can undergo further reaction(s) to afford desired derivatives thereof, e.g., epsilon caprolactone. This invention also relates in part to reaction mixtures containing one or more substituted or unsubstituted 1,6-hexanediols as principal product(s) of reaction.

16 Claims, No Drawings

OTHER PUBLICATIONS

J.K. MacDougall, et al., *Direct formation of alcohols by hydrocarbonylation of alkenes under mild conditions using rhodium trialkylphosphine catalysts* Sep., 1995.

M.C. Simpson, D.J. Cole Hamilton/Coordination Chemistry Reviews 155 (1996) 163–207 pp. 186–207.

Chem Abstracts 1972, 77, 125982t–Catalytic hydroformylation of olefins Lawrenceson, Malcolm John (BP Chemicals Ltd.).

Chem. Abstracts 1969, 71, 1,812,504, Hydroformylation of olefins, Larenceson, Malcolm.

* cited by examiner

PROCESSES FOR PRODUCING 1,6-HEXANEDIOLS

This application claims the benefit of provisional U.S. patent application Ser. Nos. 60/016,287, 60/015,952, 60/016,179 and 60/016,129, all filed Apr. 24, 1996, and all of the disclosures of which are incorporated herein by reference.

BRIEF SUMMARY OF THE INVENTION

1. Technical Field

This invention relates in part to processes for selectively producing one or more substituted or unsubstituted 1,6-hexanediols. This invention also relates in part to reaction mixtures containing one or more substituted or unsubstituted 1,6-hexanediols as the desired product(s) of reaction.

2. Background of the Invention 1,6-Hexanediol is a valuable intermediate which is useful, for example, in the production of polyesters. The processes currently used to produce 1,6-hexanediols have various disadvantages. For example, the starting materials used to produce 1,6-hexanediols are relatively expensive. In addition, the selectivity to 1,6-hexanediols in prior art processes has been low. Accordingly, it would be desirable to selectively produce 1,6-hexanediols from a relatively inexpensive starting material and by a process which can be employed commercially.

DISCLOSURE OF THE INVENTION

It has been discovered that alcohols possessing internal olefinic unsaturation can be converted to linear diols. In particular, it has been surprisingly discovered that penten-1-ols, e.g., 3-penten-1-ols, can be converted to linear 1,6-hexanediols, e.g., 1,6-hexanediol, by employing catalysts having reductive hydroformylation/isomerization capabilities.

This invention relates to processes for producing one or more substituted or unsubstituted 1,6-hexanediols, e.g., 1,6-hexanediol, which comprise subjecting one or more substituted or unsubstituted penten-1-ols to reductive hydroformylation in the presence of a reductive hydroformylation catalyst, e.g., a metal-organophosphorus ligand complex catalyst, to produce said one or more substituted or unsubstituted 1,6-hexanediols.

This invention also relates to processes for producing one or more substituted or unsubstituted 1,6-hexanediols, e.g., 1,6-hexanediol, which comprise subjecting one or more substituted or unsubstituted pentenals to reductive hydroformylation in the presence of a reductive hydroformylation catalyst, e.g., a metal-organophosphorus ligand complex catalyst, to produce said one or more substituted or unsubstituted 1,6-hexanediols.

This invention further relates to processes for producing one or more substituted or unsubstituted 1,6-hexanediols, e.g., 1,6-hexanediol, which comprise: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; and (b) subjecting said one or more substituted or unsubstituted penten-1-ols to reductive hydroformylation in the presence of a reductive hydroformylation catalyst, e.g., a metal-organophosphorus ligand complex catalyst, to produce said one or more substituted or unsubstituted 1,6-hexanediols. The reductive hydroformylation reaction conditions in steps (a) and (b) may be the same or different and the reductive hydroformylation catalysts in steps (a) and (b) may be the same or different.

This invention yet further relates to processes for selectively producing one or more substituted or unsubstituted 1,6-hexanediols, e.g., 1,6-hexanediol, which comprise: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; and (c) subjecting said one or more substituted or unsubstituted penten-1-ols to reductive hydroformylation in the presence of a reductive hydroformylation catalyst, e.g., a metal-organophosphorus ligand complex catalyst, to produce said one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in step (a), the hydrogenation reaction conditions in step (b) and the reductive hydroformylation reaction conditions in step (c) may be the same or different. The hydroformylation catalyst in step (a), the hydrogenation catalyst in step (b) and the reductive hydroformylation catalyst in step (c) may be the same or different.

This invention also relates to processes for selectively producing one or more substituted or unsubstituted 1,6-hexanediols, e.g., 1,6-hexanediol, which comprise: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; (b) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (c) subjecting said one or more substituted or unsubstituted 6-hydroxyhexanals to hydrogenation in the presence of a hydrogenation catalyst to produce said one or more substituted or unsubstituted 1,6-hexanediols. The reductive hydroformylation reaction conditions in step (a), the hydroformylation reaction conditions in step (b) and the hydrogenation reaction conditions in step (c) may be the same or different. The reductive hydroformylation catalyst in step (a), the hydroformylation catalyst in step (b) and the hydrogenation catalyst in step (c) may be the same or different.

This invention further relates to processes for selectively producing one or more substituted or unsubstituted 1,6-hexanediols, e.g., 1,6-hexanediol, which comprise: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; (c) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (d) subjecting said one or more substituted or unsubstituted 6-hydroxyhexanals to hydrogenation in the presence of a hydrogenation catalyst to produce said one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (c) and the hydrogenation reaction conditions in steps (b) and (d) may be the same or different. The hydroformylation catalysts in steps (a) and (c) and the hydrogenation catalysts in steps (b) and (d) may be the same or different.

This invention yet further relates in part to a process for producing a batchwise or continuously generated reaction mixture comprising:

(1) one or more substituted or unsubstituted 1,6-hexanediols, e.g., 1,6-hexanediol;

(2) one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal; and (6) optionally one or more substituted or unsubstituted valeraldehydes;

wherein the weight ratio of component (1) to the sum of components (3), (4), (5) and (6) is greater than about 0.1, preferably greater than about 0.25, more preferably greater than about 1.0; and the weight ratio of component (2) to the sum of components (1), (3), (4), (5) and (6) is about 0 to about 100, preferably about 0.001 to about 50; which process comprises subjecting one or more substituted or unsubstituted penten-1-ols to reductive hydroformylation in the presence of a reductive hydroformylation catalyst, e.g., a metal-organophosphorus ligand complex catalyst, to produce said batchwise or continuously generated reaction mixture.

This invention also relates in part to a process for producing a batchwise or continuously generated reaction mixture comprising:

(1) one or more substituted or unsubstituted 1,6-hexanediols, e.g., 1,6-hexanediol;

(2) one or more substituted or unsubstituted pentenals, e.g., cis-2-pentenal, trans-2-pentenal, cis-3-pentenal, trans-3-pentenal and/or 4-pentenal;

(3) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(4) optionally one or more substituted or unsubstituted 6-hydroxyhexanals, e.g., 6-hydroxyhexanal;

(5) optionally one or more substituted or unsubstituted 5-hydroxypentanals and/or cyclic lactol derivatives thereof, e.g., 2-methyl-5-hydroxypentanal;

(6) optionally one or more substituted or unsubstituted 4-hydroxybutanals and/or cyclic lactol derivatives thereof, e.g., 2-ethyl-4-hydroxybutanal; and (7) optionally one or more substituted or unsubstituted valeraldehydes;

(8) optionally one or more substituted or unsubstituted pentan-1-ols;

(9) optionally one or more substituted or unsubstituted 1,6-hexanedials, e.g., adipaldehyde;

(10) optionally one or more substituted 1,5-pentanedials, e.g., 2-methylglutaraldehyde; and

(11) optionally one or more substituted 1,4-butanedials, e.g., 2,3-dimethylsuccinaldehyde and 2-ethylsuccinaldehyde; wherein the weight ratio of component (1) to the sum of components (3), (4), (5), (6), (7), (8), (9), (10) and (11) is greater than about 0.1, preferably greater than about 0.25, more preferably greater than about 1.0; and the weight ratio of component (2) to the sum of components (1), (3), (4), (5), (6), (7), (8), (9),(10) and (11) is about 0 to about 1, preferably about 0.001 to about 50;

which process comprises subjecting one or more substituted or unsubstituted pentenals to reductive hydroformylation in the presence of a reductive hydroformylation catalyst, e.g., a metal-organophosphorus ligand complex catalyst, to produce said batchwise or continuously generated reaction mixture.

This invention further relates in part to a process for producing a batchwise or continuously generated reaction mixture comprising:

(1) one or more substituted or unsubstituted 1,6-hexanediols, e.g., 1,6-hexanediol;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal;

(6) optionally one or more substituted or unsubstituted pentan-1-ols;

(7) optionally one or more substituted or unsubstituted valeraldehydes;

(8) optionally one or more substituted or unsubstituted pentenals, e.g., cis-2-pentenal, trans-2-pentenal, cis-3-pentenal, trans-3-pentenal and/or 4-pentenal;

(9) optionally one or more substituted or unsubstituted 1,6-hexanedials, e.g., adipaldehyde;

(10) optionally one or more substituted 1,5-pentanedials, e.g., 2-methylglutaraldehyde;

(11) optionally one or more substituted 1,4-butanedials, e.g., 2,3-dimethylsuccinaldehyde and 2-ethylsuccinaldehyde; and

(12) one or more substituted or unsubstituted butadienes, e.g., butadiene;

wherein the weight ratio of component (1) to the sum of components (2), (3), (4), (5), (6), (7), (8), (9), (10) and (11) is greater than about 0.1, preferably greater than about 0.25, more preferably greater than about 1.0; and the weight ratio of component (12) to the sum of components (1), (2), (3), (4), (5), (6), (7), (8), (9), (10) and (11) is about 0 to about 100 preferably about 0.001 to about 50;

which process comprises: (a) subjecting one or more substituted or unsubstituted butadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; and (b) subjecting said one or more substituted or unsubstituted penten-1-ols to reductive hydroformylation in the presence of a reductive hydroformylation catalyst, e.g., a metal-organophosphorus ligand complex catalyst, to produce said batchwise or continuously generated reaction mixture. The reductive hydroformylation reaction conditions in steps (a) and (b) may be the same or different and the reductive hydroformylation catalysts in steps (a) and (b) may be the same or different.

This invention yet further relates in part to a process for producing a batchwise or continuously generated reaction mixture comprising:

(1) one or more substituted or unsubstituted 1,6-hexanediols, e.g., 1,6-hexanediol;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal;

(6) optionally one or more substituted or unsubstituted pentan-1-ols;

(7) optionally one or more substituted or unsubstituted valeraldehydes;

(8) optionally one or more substituted or unsubstituted pentenals, e.g., cis-2-pentenal, trans-2-pentenal, cis-3-pentenal, trans-3-pentenal and/or 4-pentenal;

(9) optionally one or more substituted or unsubstituted 1,6-hexanedials, e.g., adipaldehyde;

(10) optionally one or more substituted 1,5-pentanedials, e.g., 2-methylglutaraldehyde;

(11) optionally one or more substituted 1,4-butanedials, e.g., 2,3-dimethylsuccinaldehyde and 2-ethylsuccinaldehyde; and

(12) one or more substituted or unsubstituted butadienes, e.g., butadiene;

wherein the weight ratio of component (1) to the sum of components (2), (3), (4), (5), (6), (7), (8), (9), (10) and (11) is greater than about 0.1, preferably greater than about 0.25, more preferably greater than about 1.0; and the weight ratio of component (12) to the sum of components (1), (2), (3), (4), (5), (6), (7), (8), (9), (10) and (11) is about 0 t preferably about 0.001 to about 50;

which process comprises: (a) subjecting one or more substituted or unsubstituted butadienes, e.g., butadiene, to hydroformylation in the presence of a hydroformylation catalyst, e.g., a metal-organophosphorus ligand complex catalyst, and at an butadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; and (c) subjecting said one or more substituted or unsubstituted penten-1-ols to reductive hydroformylation in the presence of a reductive hydroformylation catalyst, e.g., a metal-organophosphorus ligand complex catalyst, to produce said batchwise or continuously generated reaction mixture. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in step (a), the hydrogenation reaction conditions in step (b) and the reductive hydroformylation reaction conditions in step (c) may be the same or different. The hydroformylation catalyst in step (a), the hydrogenation catalyst in step (b) and the reductive hydroformylation catalyst in step (c) may be the same or different.

This invention also relates in part to a process for producing a batchwise or continuously generated reaction mixture comprising:

(1) one or more substituted or unsubstituted 1,6-hexanediols, e.g., 1,6-hexanediol;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal;

(6) optionally one or more substituted or unsubstituted pentan-1-ols;

(7) optionally one or more substituted or unsubstituted valeraldehydes;

(8) optionally one or more substituted or unsubstituted pentenals, e.g., cis-2-pentenal, trans-2-pentenal, cis-3-pentenal, trans-3-pentenal and/or 4-pentenal;

(9) optionally one or more substituted or unsubstituted 1,6-hexanedials, e.g., adipaldehyde;

(10) optionally one or more substituted 1,5-pentanedials, e.g., 2-methylglutaraldehyde;

(11) optionally one or more substituted 1,4-butanedials, e.g., 2,3-dimethylsuccinaldehyde and 2-ethylsuccinaldehyde; and

(12) one or more substituted or unsubstituted butadienes, e.g., butadiene;

wherein the weight ratio of component (1) to the sum of components (2), (3), (4), (5), (6), (7), (8), (9), (10) and (11) is greater than about 0.1, preferably greater than about 0.25, more preferably greater than about 1.0; and the weight ratio of component (12) to the sum of components (1), (2), (3), (4), (5), (6), (7), (8), (9), (10) and (11) is about 0 to about 100 preferably about 0.001 to about 50;

which process comprises: (a) subjecting one or more substituted or unsubstituted butadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; (b) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (c) subjecting said one or more substituted or unsubstituted 6-hydroxyhexanals to hydrogenation in the presence of a hydrogenation catalyst to produce said batchwise or continuously generated reaction mixture. The reductive hydroformylation reaction conditions in step (a), the hydroformylation reaction conditions in step (b) and the hydrogenation reaction conditions in step (c) may be the same or different. The reductive hydroformylation catalyst in step (a), the hydroformylation catalyst in step (b) and the hydrogenation catalyst in step (c) may be the same or different.

This invention further relates in part to a process for producing a batchwise or continuously generated reaction mixture comprising:

(1) one or more substituted or unsubstituted 1,6-hexanediols, e.g., 1,6-hexanediol;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal;

(6) optionally one or more substituted or unsubstituted pentan-1-ols;

(7) optionally one or more substituted or unsubstituted valeraldehydes;

(8) optionally one or more substituted or unsubstituted pentenals, e.g., cis-2-pentenal, trans-2-pentenal, cis-3-pentenal, trans-3-pentenal and/or 4-pentenal;

(9) optionally one or more substituted or unsubstituted 1,6-hexanedials, e.g., adipaldehyde;

(10) optionally one or more substituted 1,5-pentanedials, e.g., 2-methylglutaraldehyde;

(11) optionally one or more substituted 1,4-butanedials, e.g., 2,3-dimethylsuccinaldehyde and 2-ethylsuccinaldehyde; and

(12) one or more substituted or unsubstituted butadienes, e.g., butadiene;

wherein the weight ratio of component (1) to the sum of components (2), (3), (4), (5), (6), (7), (8), (9), (10) and (11) is greater than about 0.1, preferably greater than about 0.25, more preferably greater than about 1.0; and the weight ratio of component (12) to the sum of components (1), (2), (3), (4), (5), (6), (7), (8), (9), (10) and (11) is about 0 to about 100 preferably about 0.001 to about 50;

which process comprises: (a) subjecting one or more substituted or unsubstituted butadienes, e.g., butadiene, to hydroformylation in the presence of a hydroformylation catalyst, e.g., a metal-organophosphorus ligand complex catalyst, and at an butadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; (c) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (d) subjecting said one or more substituted or unsubstituted 6-hydroxyhexanals to hydrogenation in the presence of a hydrogenation catalyst to produce said batchwise or continuously generated reaction mixture. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (c) and the hydrogenation reaction conditions in steps (b) and (d) may be the same or different. The hydroformylation catalysts in steps (a) and (c) and the hydrogenation catalysts in steps (b) and (d) may be the same or different.

This invention yet further relates to a process for producing a reaction mixture comprising one or more substituted or unsubstituted 1,6-hexanediols, e.g., 1,6-hexanediol, which process comprises subjecting one or more substituted or unsubstituted penten-1-ols to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols.

This invention also relates to a process for producing a reaction mixture comprising one or more substituted or unsubstituted 1,6-hexanediols, e.g., 1,6-hexanediol, which process comprises subjecting one or more substituted or unsubstituted pentenals to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols.

This invention further relates to a process for producing a reaction mixture comprising one or more substituted or unsubstituted 1,6-hexanediols, e.g., 1,6-hexanediol, which process comprises: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; and (b) subjecting said one or more substituted or unsubstituted penten-1-ols to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols. The reductive hydroformylation reaction conditions in steps (a) and (b) may be the same or different and the reductive hydroformylation catalysts in steps (a) and (b) may be the same or different.

This invention yet further relates to a process for producing a reaction mixture comprising one or more substituted or unsubstituted 1,6-hexanediols, e.g., 1,6-hexanediol, which process comprises: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; and (c) subjecting said one or more substituted or unsubstituted penten-1-ols to hydroformylation in the presence of a hydroformylation catalyst, e.g., a metal-organophosphorus ligand complex catalyst, to produce said reaction mixture comprising one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in step (a), the hydrogenation reaction conditions in step (b) and the reductive hydroformylation reaction conditions in step (c) may be the same or different. The hydroformylation catalyst in step (a), the hydrogenation catalyst in step (b) and the reductive hydroformylation catalyst in step (c) may be the same or different.

This invention also relates to a process for producing a reaction mixture comprising one or more substituted or unsubstituted 1,6-hexanediols, e.g., 1,6-hexanediol, which process comprises: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; (b) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (c) subjecting said one or more substituted or unsubstituted 6-hydroxyhexanals to hydrogenation in the presence of a hydrogenation catalyst to produce said reaction mixture comprising one or more substituted or unsubstituted 1,6-hexanediols. The reductive hydroformylation reaction conditions in step (a), the hydroformylation reaction conditions in step (b) and the hydrogenation reaction conditions in step (c) may be the same or different. The reductive hydroformylation catalyst in step (a), the hydroformylation catalyst in step (b) and the hydrogenation catalyst in step (c) may be the same or different.

This invention further relates to a process for producing a reaction mixture comprising one or more substituted or unsubstituted 1,6-hexanediols, e.g., 1,6-hexanediol, which process comprises: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; (c) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (d) subjecting said one or more substituted or unsubstituted 6-hydroxyhexanals to hydrogenation in the presence of a hydrogenation catalyst to produce said reaction mixture comprising one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (c) and the hydrogenation reaction conditions in steps (b) and (d) may be the same or different. The hydroformylation catalysts in steps (a) and (c) and the hydrogenation catalysts in steps (b) and (d) may be the same or different.

The processes of this invention can achieve high selectivities of alkadienes, pentenals and penten-1-ols to 1,6-hexanediols, i.e., selectivities of alkadienes to 1,6-hexanediols of at least 10% by weight and up to 85% by weight or greater may be achieved by the processes of this invention.

This invention yet further relates in part to a batchwise or continuously generated reaction mixture comprising:

(1) one or more substituted or unsubstituted 1,6-hexanediols, e.g., 1,6-hexanediol;
(2) one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;
(3) optionally one or more substituted or unsubstituted 6-hydroxyhexanals, e.g., 6-hydroxyhexanal;
(4) optionally one or more substituted or unsubstituted 5-hydroxypentanals and/or cyclic lactol derivatives thereof, e.g., 2-methyl-5-hydroxypentanal;
(5) optionally one or more substituted or unsubstituted 4-hydroxybutanals and/or cyclic lactol derivatives thereof, e.g., 2-ethyl-4-hydroxybutanal; and
(6) optionally one or more substituted or unsubstituted valeraldehydes;

wherein the weight ratio of component (1) to the sum of components (3), (4), (5) and (6) is greater than about 0.1, preferably greater than about 0.25, more preferably greater than about 1.0; and the weight ratio of component (2) to the sum of components (1), (3), (4), (5) and (6) is about 0 to about 100, preferably about 0.001 to about 50.

This invention also relates in part to a batchwise or continuously generated reaction mixture comprising:

(1) one or more substituted or unsubstituted 1,6-hexanediols, e.g., 1,6-hexanediol;
(2) one or more substituted or unsubstituted pentenals, e.g., cis-2-pentenal, trans-2-pentenal, cis-3-pentenal, trans-3-pentenal and/or 4-pentenal;
(3) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;
(4) optionally one or more substituted or unsubstituted 6-hydroxyhexanals, e.g., 6-hydroxyhexanal;
(5) optionally one or more substituted or unsubstituted 5-hydroxypentanals and/or cyclic lactol derivatives thereof, e.g., 2-methyl-5-hydroxypentanal;
(6) optionally one or more substituted or unsubstituted 4-hydroxybutanals and/or cyclic lactol derivatives thereof, e.g., 2-ethyl-4-hydroxybutanal; and
(7) optionally one or more substituted or unsubstituted valeraldehydes;
(8) optionally one or more substituted or unsubstituted pentan-1-ols;
(9) optionally one or more substituted or unsubstituted 1,6-hexanedials, e.g., adipaldehyde;
(10) optionally one or more substituted 1,5-pentanedials, e.g., 2-methylglutaraldehyde; and
(11) optionally one or more substituted 1,4-butanedials, e.g., 2,3-dimethylsuccinaldehyde and 2-ethylsuccinaldehyde;

wherein the weight ratio of component (1) to the sum of components (3), (4), (5), (6), (7), (8), (9), (10) and (11) is greater than about 0.1, preferably greater than about 0.25, more preferably greater than about 1.0; and the weight ratio of component (2) to the sum of components (1), (3), (4), (5), (6), (7), (8), (9), (10) and (11) is about 0 to about 100, preferably about 0.001 to about 50.

This invention further relates in part to a batchwise or continuously generated reaction mixture comprising:

(1) one or more substituted or unsubstituted 1,6-hexanediols, e.g., 1,6-hexanediol;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 6-hydroxyhexanals, e.g., 6-hydroxyhexanal;

(4) optionally one or more substituted or unsubstituted 5-hydroxypentanals and/or cyclic lactol derivatives thereof, e.g., 2-methyl-5-hydroxypentanal;

(5) optionally one or more substituted or unsubstituted 4-hydroxybutanals and/or cyclic lactol derivatives thereof, e.g., 2-ethyl-4-hydroxybutanal;

(6) optionally one or more substituted or unsubstituted pentan-1-ols;

(7) optionally one or more substituted or unsubstituted valeraldehydes;

(8) optionally one or more substituted or unsubstituted pentenals, e.g., cis-2-pentenal, trans-2-pentenal, cis-3-pentenal, trans-3-pentenal and/or 4-pentenal;

(9) optionally one or more substituted or unsubstituted 1,6-hexanedials, e.g., adipaldehyde;

(10) optionally one or more substituted 1,5-pentanedials, e.g., 2-methylglutaraldehyde;

(11) optionally one or more substituted 1,4-butanedials, e.g., 2,3-dimethylsuccinaldehyde and 2-ethylsuccinaldehyde; and

(12) one or more substituted or unsubstituted butadienes, e.g., butadiene;

wherein the weight ratio of component (1) to the sum of components (2), (3), (4), (5), (6), (7), (8), (9), (10) and (11) is greater than about 0.1, preferably greater than about 0.25, more preferably greater than about 1.0; and the weight ratio of component (12) to the sum of components (1), (2), (3), (4), (5), (6), (7), (8), (9), (10) and (11) is about 0 to about 100, preferably about 0.001 to about 50.

This invention yet further relates in part to a reaction mixture comprising one or more substituted or unsubstituted 1,6-hexanediols, e.g., 1,6-hexanediol, in which said reaction mixture is prepared by a process which comprises subjecting one or more substituted or unsubstituted penten-1-ols to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols.

This invention also relates in part to a reaction mixture comprising one or more substituted or unsubstituted 1,6-hexanediols, e.g., 1,6-hexanediol, in which said reaction mixture is prepared by a process which comprises subjecting one or more substituted or unsubstituted pentenals to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols.

This invention further relates in part to a reaction mixture comprising one or more substituted or unsubstituted 1,6-hexanediols, e.g., 1,6-hexanediol, in which said reaction mixture is prepared by a process which comprises: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; and (b) subjecting said one or more substituted or unsubstituted penten-1-ols to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols. The reductive hydroformylation reaction conditions in steps (a) and (b) may be the same or different and the hydroformylation catalysts in steps (a) and (b) may be the same or different.

This invention yet further relates in part to a reaction mixture comprising one or more substituted or unsubstituted 1,6-hexanediols, e.g., 1,6-hexanediol, in which said reaction mixture is prepared by a process which comprises: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; and (c) subjecting said one or more substituted or unsubstituted penten-1-ols to reductive hydroformylation in the presence of a reductive hydroformylation catalyst, e.g., a metal-organophosphorus ligand complex catalyst, to produce said reaction mixture comprising one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in step (a), the hydrogenation reaction conditions in step (b) and the reductive hydroformylation reaction conditions in step (c) may be the same or different. The hydroformylation catalyst in step (a), the hydrogenation catalyst in step (b) and the reductive hydroformylation catalyst in step (c) may be the same or different.

This invention also relates in part to a reaction mixture comprising one or more substituted or unsubstituted 1,6-hexanediols, e.g., 1,6-hexanediol, in which said reaction mixture is prepared by a process which comprises: (a) subjecting one or more substituted or unsubstituted alkadienes, e.g., butadiene, to reductive hydroformylation in the presence of a reductive hydroformylation catalyst, e.g., a metal-organophosphorus ligand complex catalyst, to produce one or more substituted or unsubstituted penten-1-ols; (b) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (c) subjecting said one or more substituted or unsubstituted 6-hydroxyhexanals to hydrogenation in the presence of a hydrogenation catalyst to produce said reaction mixture comprising one or more substituted or unsubstituted 1,6-hexanediols. The reductive hydroformylation reaction conditions in step (a), the hydroformylation reaction conditions in step (b) and the hydrogenation reaction conditions in step (c) may be the same or different. The reductive hydroformylation catalyst in step (a), the hydroformylation catalyst in step (b) and the hydrogenation catalyst in step (c) may be the same or different.

This invention further relates in part to a reaction mixture comprising one or more substituted or unsubstituted 1,6-hexanediols, e.g., 1,6-hexanediol, in which said reaction mixture is prepared by a process which comprises: (a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted pentenals; (b) subjecting said one or more substituted or unsubstituted pentenals to hydrogenation in the presence of a hydrogenation catalyst to produce one or more substituted or unsubstituted penten-1-ols; (c) subjecting said one or more substituted or unsubstituted penten-1-ols to hydroformylation in the presence of a hydroformylation catalyst, e.g., a metal-organophosphorus ligand complex catalyst, to produce one or more substituted or unsubstituted 6-hydroxyhexanals; and (d) subjecting said one or more substituted or unsubstituted 6-hydroxyhexanals to hydrogenation in the presence of a hydrogenation catalyst to produce said reaction mixture comprising one or more substituted or unsubstituted 1,6-hexanediols. In a preferred embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (c) and the hydrogenation reaction conditions in steps (b) and (d) may be the same or different. The hydroformylation catalysts in steps (a) and (c) and the hydrogenation catalysts in steps (b) and (d) may be the same or different.

The reaction mixtures of this invention are distinctive insofar as the processes for their preparation achieve the generation of high selectivities of 1,6-hexanediols in a manner which can be suitably employed in a commercial process for the manufacture of 1,6-hexanediols. In particular, the reaction mixtures of this invention are distinctive insofar as the processes for their preparation allow for the production of 1,6-hexanediols in relatively high yields without generating large amounts of byproducts, e.g., pentanols and 2-methyl-1,5-pentanediols.

DETAILED DESCRIPTION

The reductive hydroformylation processes of this invention include, but are not limited to, converting one or more substituted or unsubstituted penten-1-ols to one or more substituted or unsubstituted 1,6-hexanediols, converting one or more substituted or unsubstituted pentenals to one or more substituted or unsubstituted 1,6-hexanediols, and converting one or more substituted or unsubstituted alkadienes to one or more substituted or unsubstituted penten-1-ols and/or 1,6-hexanediols. As used herein, the term "reductive hydroformylation" is contemplated to include, but is not limited to, all permissible hydroformylation, hydrogenation and isomerization processes which include converting one or more substituted or unsubstituted penten-1-ols to one or more substituted or unsubstituted 1,6-hexanediols, converting one or more substituted or unsubstituted pentenals to one or more substituted or unsubstituted 1,6-hexanediols, and converting one or more substituted or unsubstituted alkadienes to one or more substituted or unsubstituted penten-1-ols and/or 1,6-hexanediols. In general, the reductive hydroformylation step or stage comprises reacting one or more substituted or unsubstituted penten-1-ols with carbon monoxide and hydrogen in the presence of a catalyst to produce one or more substituted or unsubstituted 1,6-hexanediols, reacting one or more substituted or unsubstituted pentenals with carbon monoxide and hydrogen in the presence of a catalyst to produce one or more substituted or unsubstituted 1,6-hexanediols, and reacting one or more substituted or unsubstituted alkadienes with carbon monoxide and hydrogen in the presence of a catalyst to produce one or more substituted or unsubstituted penten-1-ols and/or 1,6-hexanediols.

The reductive hydroformylation processes of this invention may be conducted in one or more steps or stages, preferably a one step process. The hydroformylation, hydrogenation and isomerization reactions may be conducted in any permissible sequence so as to produce one or more substituted or unsubstituted 1,6-hexanediols or penten-1-ols.

Illustrative hydroformylation stages include, but are not limited to, the following: (a) converting one or more substituted or unsubstituted alkadienes to one or more substituted or unsubstituted pentenals; and (b) converting one or more substituted or unsubstituted penten-1-ols to one or more substituted or unsubstituted 6-hydroxyhexanals.

Illustrative hydrogenation stages include, but are not limited to, the following: (a) converting one or more substituted or unsubstituted pentenals to one or more substituted or unsubstituted penten-1-ols; and (b) converting one or more substituted or unsubstituted 6-hydroxyhexanals to one or more substituted or unsubstituted 1,6-hexanediols.

Illustrative isomerization stages include, but are not limited to, the following: (a) converting one or more substituted or unsubstituted 2-pentenals and/or 3-pentenals to one or more substituted or unsubstituted 4-pentenals, and (b) converting one or more substituted or unsubstituted 2-penten-1-ols and/or 3-penten-1-ols to one or more substituted or unsubstituted 4-penten-1-ols.

Suitable reductive hydroformylation reaction conditions and processing techniques and suitable reductive hydroformylation catalysts include those described below for the hydroformylation and hydrogenation steps or stages. The hydroformylation and hydrogenation steps or stages employed in the processes of this invention may be carried out as described below.

While not wishing to be bound to any particular reaction mechanism, it is believed that the overall reductive hydroformylation reaction generally proceeds in one or more steps or stages. This invention is not intended to be limited in any manner by any particular reaction mechanism, but rather encompasses all permissible hydroformylation, hydrogenation and isomerization processes as described herein.

Hydroformylation Steps or Stages

The hydroformylation processes involve the production of aldehydes, e.g., 6-hydroxyhexanals or pentenals, by reacting an olefinic compound, e.g., penten-1-ols, or an alkadiene, with carbon monoxide and hydrogen in the presence of a metal-ligand complex catalyst and optionally free ligand in a liquid medium that also contains a solvent for the catalyst and ligand. The processes may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, the term "hydroformylation" is contemplated to include, but is not limited to, all permissible hydroformylation processes which involve converting one or more substituted or unsubstituted olefinic compounds or alkadienes to one or more substituted or unsubstituted aldehydes. In general, the hydroformylation step or stage comprises reacting one or more substituted or unsubstituted penten-1-ols with carbon monoxide and hydrogen in the presence of a catalyst to produce one or more substituted or unsubstituted 6-hydroxyhexanals, reacting one or more substituted or unsubstituted alkadienes with carbon monoxide and hydrogen in the presence of a catalyst to produce one or more substituted or unsubstituted pentenals, and reacting one or more substituted or unsubstituted alkadienes or pentenals with carbon monoxide and hydrogen in the presence of a catalyst to produce one or more substituted or unsubstituted 1,6-hexanediols.

The hydroformylation reaction mixtures employable herein includes any solution derived from any corresponding hydroformylation process that may contain at least some amount of four different main ingredients or components, i.e., the aldehyde product, a metal-ligand complex catalyst, optionally free ligand and an organic solubilizing agent for said catalyst and said free ligand, said ingredients corresponding to those employed and/or produced by the hydroformylation process from whence the hydroformylation reaction mixture starting material may be derived. By "free ligand" is meant ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin or alkadiene starting material, carbon monoxide and hydrogen gases, and in situ formed type products, such as saturated hydrocarbons and/or unreacted isomerized or olefins corresponding to the olefin or alkadiene starting materials, and high boiling liquid aldehyde condensation byproducts, as well as other inert co-solvent type materials or hydrocarbon additives, if employed.

The catalysts useful in the hydroformylation process include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. 08/918-718, filed Mar. 10, 1997, the disclosure of which is incorporated herein by reference. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $BF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydroformylation reactions that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substitutent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, e.g., alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; ionic radicals such as —$SO_3M$ wherein M represents inorganic or organic cationic atoms or radicals; sulfonyl radicals such as —$SO_2R^2$; ether radicals such as —$OR^2$; sulfinyl radicals such as —$SOR^2$; sulfenyl radicals such as —$SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —$N(R^2)_2$, each $R^2$ taken together can also represent a divalent bridging group that forms a heterocyclic radical with the nitrogen atom and in amido substituents such as $C(O)N(R^2)_2$ and —$N(R^2)C(O)R^2$ each —$R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(-)-O-isopropylidene-2,3-dihydroxy-1,4-bis(diphenylphosphino) butane and/or (4S,5S)-(+)-O-isopropylidene-2,3-dihydroxy-1,4-bis(diphenylphosphino)butane and/or (4S,5R)-(-)-O-isopropylidene-2,3-dihydroxy-1,4-bis(diphenylphosphino) butane, substituted or unsubstituted bicyclic bisphosphines such as 1,2-bis(1,4-cyclooctylenephosphino)ethane, 1,3-bis (1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, xantphos, thixantphos, bis(diphenylphosphino)ferrocene, bis(diisopropylphosphino)ferrocene, bis (diphenylphosphino)ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749, 4,861,918; 4,694,109; 4,742,178; 4,851,581; 4,824,977; 5,332,846; 4,774,362; and WO Patent Application Ser. No. 95/30680, published Nov. 16, 1995; the disclosures of which are incorporated herein by reference.

The organophosphites that may serve as the ligand of the metal-organophosphite ligand complex catalyst and/or free ligand of the processes and reaction product mixtures of this invention may be of the achiral (optically inactive) or chiral (optically active) type and are well known in the art.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

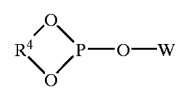

(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos. 3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

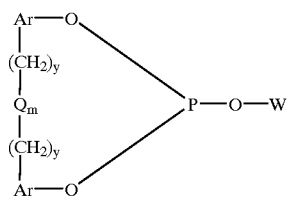

(IV)

wherein W is as defined above, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^6-$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

(V)

wherein each $R^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for $R^1$ in formula (I).

Representative organopolyphosphites contain two or more tertiary (trivalent) phosphorus atoms and may include those having the formula:

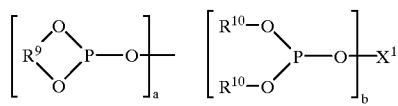

(VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

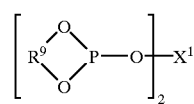

(VII)

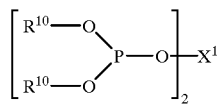

(VIII)

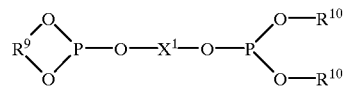

(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741;

5,264,616; 5,312,996; 5,364,950; and 5,391,801; the disclosures of all of which are incorporated herein by reference.

Representative of more preferred classes of organobisphosphites are those of the following formulas (X) to (XII):

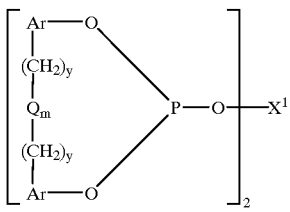

(X)

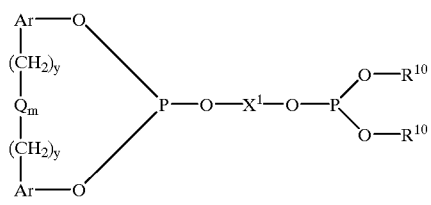

(XI)

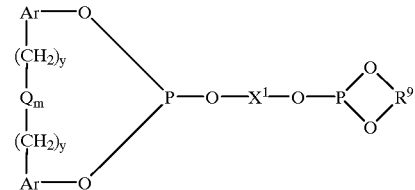

(XII)

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —C($R^5$)$_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$,— is bonded to said phenylene radicals in positions that are ortho to the oxygen atoms of the formulas that connect the phenylene radicals to their phosphorus atom of the formulas. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

—$SO_3M$ wherein M represents inorganic or organic cation,

—$PO_3M$ wherein M represents inorganic or organic cation,

—$N(R^{11})_3X^2$ wherein each $R^{11}$ is the same or different and represents a hydrocarbon radical containing from 1 to 30 carbon atoms, e.g, alkyl, aryl, alkaryl, aralkyl, and cycloalkyl radicals, and $X^2$ represents inorganic or organic anion, —$CO_2M$ wherein M represents inorganic or organic cation, as described, e.g., in U.S. Pat. Nos. 5,059,710; 5,113,022, 5,114,473 and 5,449,653, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and $X^2$, for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation, quaternary ammonium cations, phosphonium cations, arsonium cations and iminium cations. Suitable anionic groups include, for example, sulfate, carbonate, phosphate, chloride, acetate, oxalate and the like.

Of course any of the $R^9$, $R^{10}$, $X^2$ and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si($R^{12}$)$_3$; amino radicals such as —N($R^{12}$)$_2$; phosphine radicals such as -aryl-P($R^{12}$)$_2$; acyl radicals such as —C(O)$R^{12}$; acyloxy radicals such as —OC(O)$R^{12}$; amido radicals such as —CON($R^{12}$)$_2$ and —N($R^{12}$)COR$^{12}$; sulfonyl radicals such as —$SO_2R^{12}$; alkoxy radicals such as —$OR^{12}$; sulfinyl radicals such as —$SOR^{12}$; sulfenyl radicals such as —$SR^{12}$; phosphonyl radicals such as —P(O)($R^{12}$)$_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N($R^{12}$)$_2$ each $R^{12}$ taken together can also represent a divalent bridging group that forms a heterocyclic radical with the nitrogen atom, and in amido substituents such as —C(O)N($R^{12}$)$_2$ and —N($R^{12}$)COR$^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following:

2-t-butyl-4-methoxyphenyl(3,3'-di-t-butyl-5,5'-dimethoxy-1,1'-biphenyl-2,2'-diyl)phosphite having the formula:

Ligand A

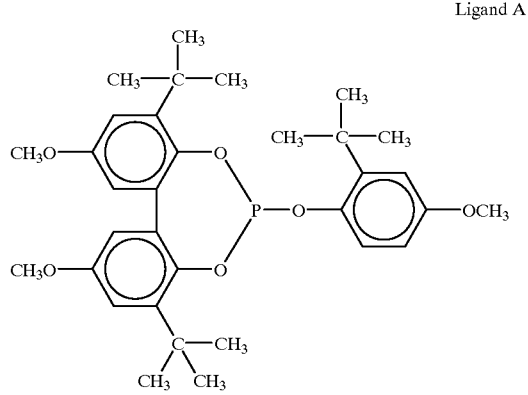

methyl(3,3'-di-t-butyl-5,5'-dimethoxy-1,1'-biphenyl-2,2'-diyl)phosphite having the formula:

Ligand B

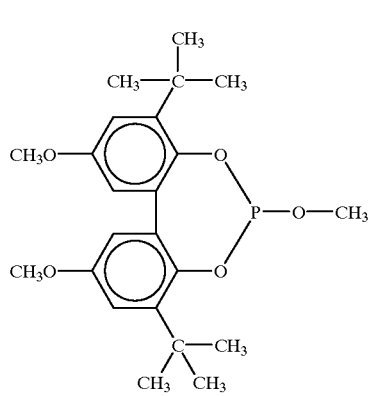

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

Ligand C

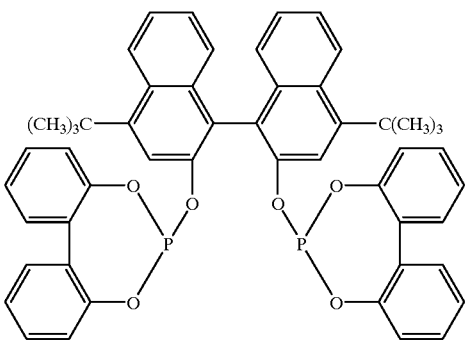

6,6'-[[3,3'-bis(1,1-dimethylethyl)-5,5'-dimethoxy-[1,1'-biphenyl]-2,2'-diyl]bis(oxy)]bis-dibenzo[d,f][1,3,2] dioxaphosphepin having the formula:

Ligand D

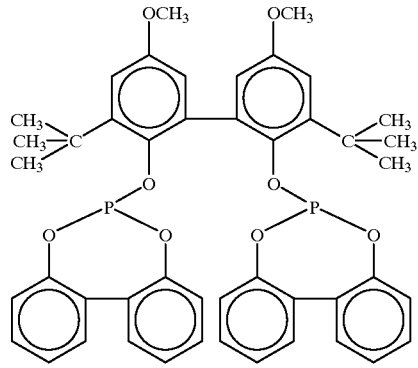

6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

Ligand E

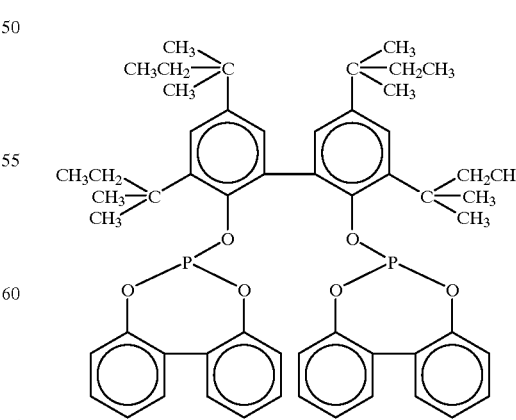

6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

Ligand F

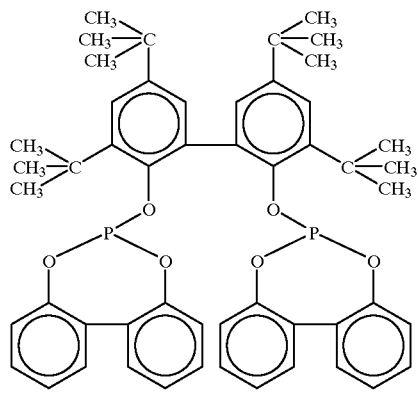

(2R,4R)-di[2,2'-(3,3',5,5'-tetrakis-tert-amyl-1,1'-biphenyl)]-2,4-pentyldiphosphite having the formula:

Ligand G

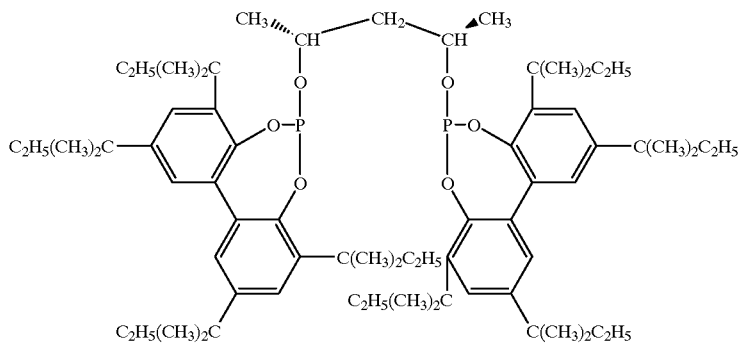

(2R,4R)-di[2,2'-(3,3',5,5'-tetrakis-tert-butyl-1,1'-biphenyl)]-2,4-pentyldiphosphite having the formula:

Ligand H

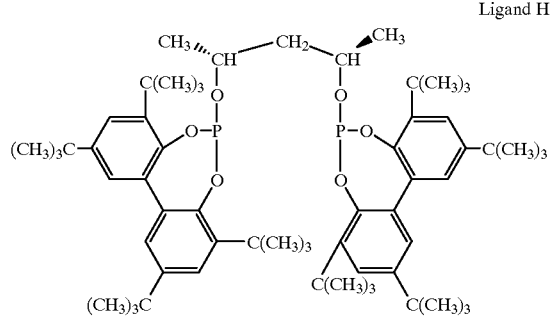

(2R,4R)-di[2,2'-(3,3'-di-amyl-5,5'-dimethoxy-1,1'-biphenyl)]-2,4-pentyldiphosphite having the formula:

Ligand I

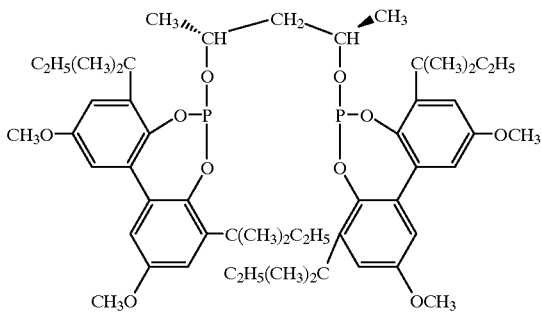

(2R,4R)-di[2,2'-(3,3'-di-tert-butyl-5,5'-dimethyl-1,1'-biphenyl)]-2,4-pentyldiphosphite having the formula:

Ligand J

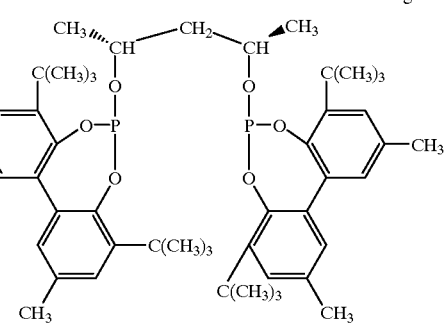

(2R,4R)-di[2,2'-(3,3'-di-tert-butyl-5,5'-diethoxy-1,1'-biphenyl)]-2,4-pentyldiphosphite having the formula:

Ligand K

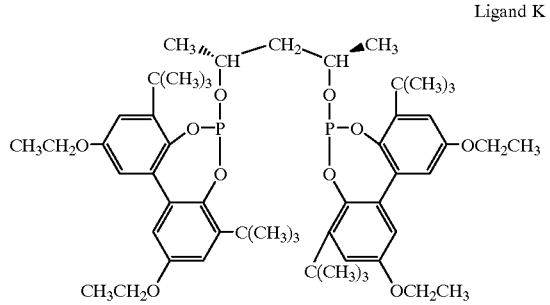

(2R,4R)-di[2,2'-(3,3'-di-tert-butyl-5,5'-diethyl-1,1'-biphenyl)]-2,4-pentyldiphosphite having the formula:

Ligand L

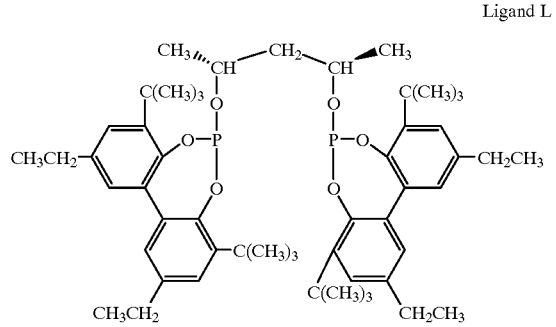

(2R,4R)-di[2,2'-(3,3'-di-tert-butyl-5,5'-dimethoxy-1,1'-biphenyl)]-2,4-pentyldiphosphite having the formula:

Ligand M

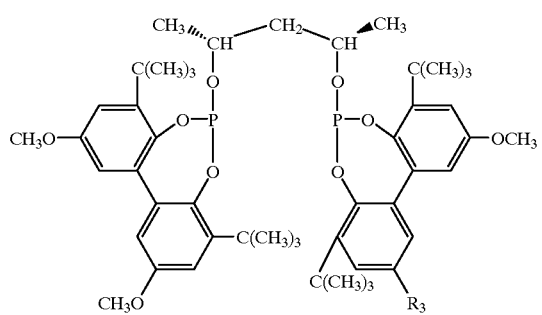

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand N

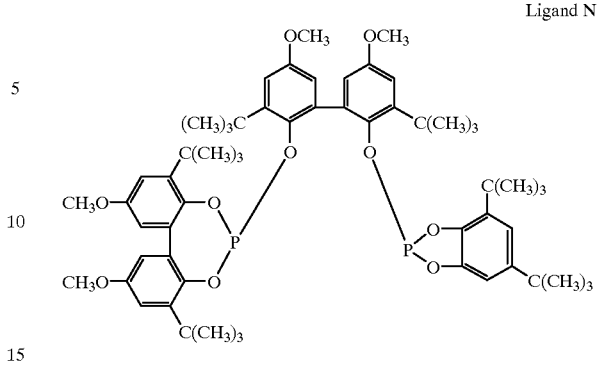

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand O

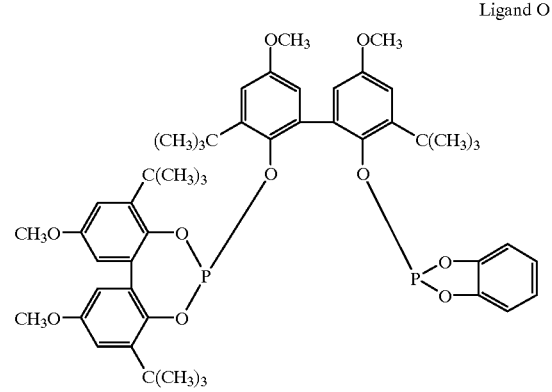

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand P

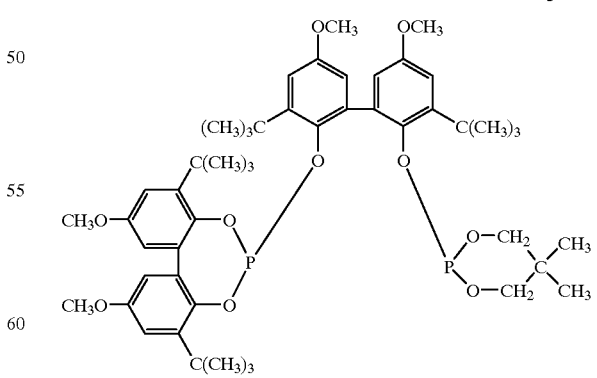

2'-[[4,8-bis(1,1-dimethylethyl)-2,10-dimethoxydibenzo[d,f][1,3,2]-dioxaphosphepin-6-yl]oxy]-3,3'-bis(1,1- dimethylethyl)-5,5'-dimethoxy[1,1'-biphenyl]-2-yl bis(4-hexylphenyl)ester of phosphorous acid having the formula:

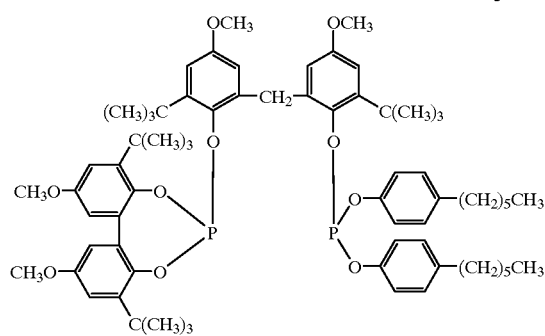

Ligand Q

2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

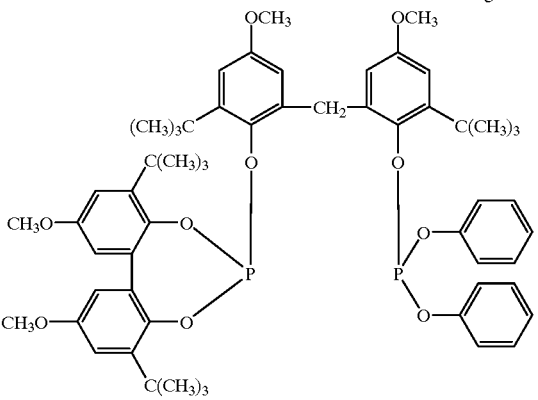

Ligand R 3-methoxy-1,3-cyclohexamethylene tetrakis[3,6-bis(1,1-dimethylethyl)-2-naphthalenyl]ester of phosphorous acid having the formula:

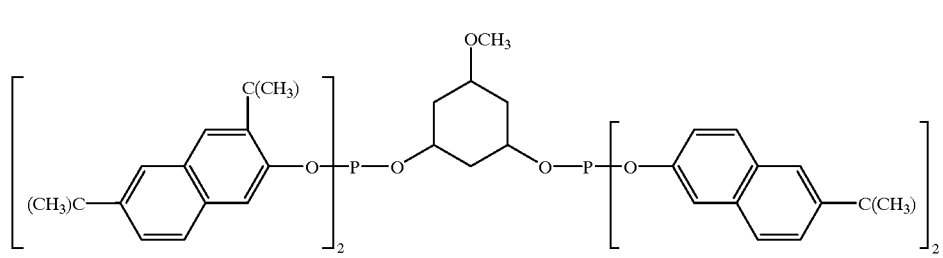

Ligand S

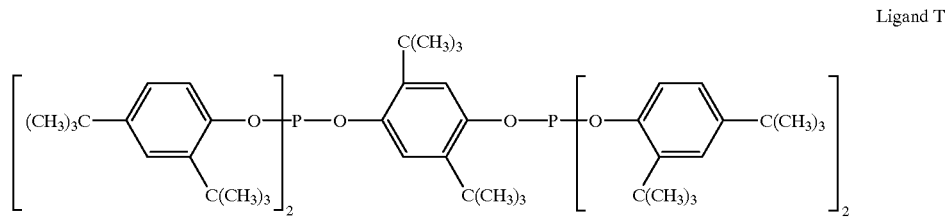

Ligand T methylenedi-2,1-phenylene tetrakis[2,4-bis(1,1-dimethylethyl)phenyl]ester of phosphorous acid having the formula:
2,5-bis(1,1-dimethylethyl)-1,4-phenylene tetrakis[2,4-bis(1,1-dimethylethyl)phenyl]ester of phosphorous acid having the formula:

Ligand U

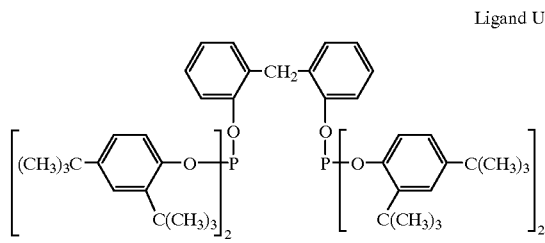

[1,1'-biphenyl]-2,2'-diyl tetrakis[2-(1,1-dimethylethyl)-4-methoxyphenyl]ester of phosphorous acid having the formula:

Ligand V

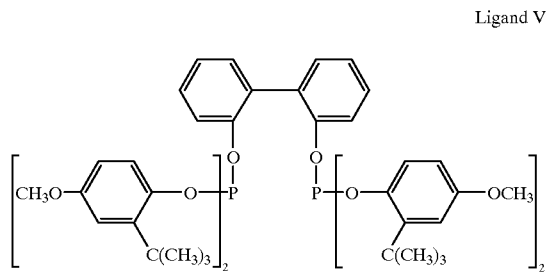

Still other illustrative organophosphorus ligands useful in this invention include those disclosed in U.S. patent application Ser. No. 08/849-389, filed on an even date herewith, the disclosure of which is incorporated herein by reference.

The metal-ligand complex catalysts employable in this invention may be formed by methods known in the art. The metal-ligand complex catalysts may be in homogeneous or heterogeneous form. For instance, preformed metal hydrido-carbonyl-organophosphorus ligand catalysts may be prepared and introduced into the reaction mixture of a hydroformylation process. More preferably, the metal-ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-ligand complex precursor catalyst, an organic solvent and free ligand. Such precursor compositions may be prepared by forming a solution of a metal starting material, such as a metal oxide, hydride, carbonyl or salt, e.g. a nitrate, which may or may not be in complex combination with a ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydroformylation process.

By way of illustration, the preferred catalyst precursor composition of this invention consists essentially of a solubilized rhodium carbonyl organophosphorus ligand complex precursor catalyst, a solvent and free organophosphorus ligand prepared by forming a solution of rhodium dicarbonyl acetylacetonate, an organic solvent and a ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. In a continuous process, the acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-ligand complex catalyst as described herein. Of course mixtures of such catalysts can also be employed if desired. Mixtures of hydroformylation catalysts and hydrogenation catalysts described below may also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the organophosphorus ligand concentration in hydroformylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the rhodium metal) may also be present in the hydroformylation reaction medium. The free ligand may correspond to any of the above-defined ligands discussed above as employable herein. It is preferred that the free ligand be the same as the ligand of the metal-ligand complex catalyst employed. However, such ligands need not be the same in any given process. The hydroformylation reaction may involve up to 100 moles, or higher, of free ligand per mole of metal in the hydroformylation reaction medium. Preferably the hydroformylation reaction is carried out in the presence of from about 0.25 to about 50 moles of coordinatable phosphorus, and more preferably from about 0.5 to about 30 moles of coordinatable phosphorus, per mole of metal present in the reaction medium; said amounts of coordinatable phosphorus being the sum of both the amount of coordinatable phosphorus that is bound (complexed) to the rhodium metal present and the amount of free (non-complexed) coordinatable phosphorus present. Of course, if desired, make-up or additional coordinatable phosphorus can be supplied to the reaction medium of the hydroformylation reaction at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins or alkadienes to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The rhodium catalyst may be attached to a thin film or membrane support, such as cellulose acetate or polyphenylenesulfone, as described in for example J. Mol. Cat. 1990, 63, 213–221.

The rhodium catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported triphenylphosphine. The supported ligand is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydroformylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction may be carried out in the gas phase. More preferably, the reaction is carried out in the slurry phase due to the high boiling points of the products, and to avoid decomposition of the product aldehydes. The catalyst may then be separated from the product mixture by filtration or decantation.

The substituted and unsubstituted alkadiene starting materials useful in the hydroformylation reactions include, but are not limited to, conjugated aliphatic diolefins represented by the formula:

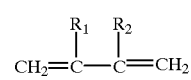

(XIII)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadiene starting materials are butadiene, isoprene, dimethyl butadiene and cyclopentadiene. Most preferably, the alkadiene starting material is butadiene itself ($CH_2$=$CH$—$CH$=$CH_2$). For purposes of this invention, the term "alkadiene" is contemplated to include all permissible substituted and unsubstituted conjugated diolefins, including all permissible mixtures comprising one or more substituted or unsubstituted conjugated diolefins. Illustrative of suitable substituted and unsubstituted alkadienes (including derivatives of alkadienes) include those permissible substituted and unsubstituted alkadienes described in Kirk-Othmer, Encyclopedia of Chemical Technology, Fourth Edition, 1996, the pertinent portions of which are incorporated herein by reference.

The hydroformylation reaction conditions may include any suitable type hydroformylation conditions heretofore employed for producing aldehydes. For instance, the total gas pressure of hydrogen, carbon monoxide and olefin or alkadiene starting compound of the hydroformylation process may range from about 1 to about 10,000 psia. In general, the hydroformylation process is operated at a total gas pressure of hydrogen, carbon monoxide and olefin or alkadiene starting compound of less than about 1500 psia and more preferably less than about 1000 psia, the minimum total pressure being limited predominately by the amount of reactants necessary to obtain a desired rate of reaction. The total pressure employed in the hydroformylation reaction may range in general from about 20 to about 3000 psia, preferably from about 50 to 1500 psia. The total pressure of the hydroformylation process will be dependent on the particular catalyst system employed.

More specifically, the carbon monoxide partial pressure of the hydroformylation process in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed.

Carbon monoxide partial pressure should be sufficient for the hydroformylation reaction, e.g., of an alkadiene to pentenal, to occur at an acceptable rate. Hydrogen partial pressure must be sufficient for the hydroformylation and/or hydrogenation reaction to occur at an acceptable rate, but not so high that hydrogenation of butadiene or isomerization of pentenals to undesired isomers occurs. It is understood that carbon monoxide and hydrogen can be employed separately, in mixture with each other, i.e., synthesis gas, or may in part be produced in situ under reaction conditions.

Further, the hydroformylation process may be conducted at a reaction temperature from about 20° C. to about 200° C. may be employed, preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), isomerization of pentenals to undesired isomers may occur.

Of course, it is to be also understood that the hydroformylation reaction conditions employed will be governed by the type of aldehyde product desired.

In the alkadiene hydroformylation step, the alkadiene hydroformylation reaction may be conducted at an alkadiene conversion and/or carbon monoxide partial pressure sufficient to selectively produce the pentenals and penten-1-ols respectively. In certain cases, it has been found that if the partial pressure of carbon monoxide in the alkadiene hydroformylation reaction system is higher than the partial pressure of hydrogen, the conversion of pentenal intermediates to hydrogenated and bishydroformylated byproducts is suppressed. It is believed that these reactions are inhibited by carbon monoxide. It has also been found that when the alkadiene hydroformylation reaction is conducted with incomplete conversion of butadiene, the conversion of pentenal intermediates to bishydroformylated byproducts is suppressed. In general, the alkadiene conversion can range from about 1 weight percent to about 100 weight percent, preferably from about 10 weight percent to about 100 weight percent, and more preferably from about 25 weight percent to about 100 weight percent, based on the total weight of alkadiene fed to the reaction. While not wishing to be bound to any particular theory, it is believed that butadiene preferentially complexes with the metal-ligand complex catalyst, acting as an inhibitor to the hydroformylation of the pentenal intermediates. The partial conversion of butadiene may be accomplished by short reaction time, low total pressure, low catalyst concentration, and/or low temperature. High butadiene concentrations are especially useful in the hydroformylation processes of this invention.

In the penten-1-ol reductive hydroformylation step of this invention, the penten-1-ol reductive hydroformylation reaction can be conducted at a penten-1-ol conversion and/or carbon monoxide partial pressure sufficient to selectively produce the 1,6-hexanediols. However, in the penten-1-ol reductive hydroformylation reaction, the penten-1-ol conversion may be complete or incomplete, and the partial pressure of carbon monoxide may be higher or lower than the partial pressure of hydrogen as described above.

To enable maximum levels of 3-pentenals and/or 4-pentenals and minimize 2-pentenals, it is desirable to maintain some alkadiene partial pressure, or when the alkadiene conversion is complete, the carbon monoxide partial pressure should be sufficient to prevent or minimize derivatization, e.g., isomerization and/or hydrogenation, of substituted or unsubstituted 3-pentenals.

In an embodiment, the alkadiene hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. In another embodiment, the alkadiene, e.g., butadiene, hydroformylation is conducted at an alkadiene partial pressure of greater than 0 psi, preferably greater than 5 psi, and more preferably greater than 9 psi; and at a carbon monoxide partial pressure of greater than 0 psi, preferably greater than 25 psi, and more preferably greater than 100 psi.

The hydroformylation reaction is also conducted in the presence of water or an organic solvent for the metal-ligand complex catalyst and free ligand. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

The reductive hydroformylation process may also be conducted in the presence of a promoter. As used herein, "promoter" means an organic or inorganic compound with an ionizable hydrogen of pKa of from about 1 to about 35. Illustrative promoters include, for example, protic solvents, organic and inorganic acids, alcohols, water, phenols, thiols, thiophenols, nitroalkanes, ketones, nitriles, amines (e.g., pyrroles and diphenylamine), amides (e.g., acetamide), mono-, di- and trialkylammonium salts, and the like. The promoter may be present in the reductive hydroformylation reaction mixture either alone or incorporated into the ligand structure, either as the metal-ligand complex catalyst or as free ligand, or into the alkadiene structure. The desired promoter will depend on the nature of the ligands and metal of the metal-ligand complex catalysts. In general, a catalyst with a more basic metal-bound acyl or other intermediate will require a lower concentration and/or a less acidic promoter. In general, the amount of promoter may range from about 10 parts per million or so up to about 99 percent by weight or more based on the total weight of the reductive hydroformylation process mixture starting materials.

In an embodiment of the invention, the hydroformylation reaction mixture may consist of one or more liquid phases, e.g. a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. A well-known application of this technology is the aqueous-phase hydroformylation of olefins employing sulfonated phosphine ligands for the rhodium catalyst. A process carried out in aqueous solvent is particularly advantageous for the preparation of aldehydes because the products may be separated from the catalyst by extraction into an organic solvent. Alternatively, aldehydes, particularly pentenals, adipaldehyde and 6-hydroxyhexanal, which tend to undergo self-condensation reactions, are expected to be stabilized in aqueous solution as the aldehyde hydrates.

As described herein, the phosphorus-containing ligand for the rhodium hydroformylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of the process of this invention, an olefin can be hydroformylated along with a alkadiene using the above-described metal-ligand complex catalysts. In such cases, an aldehyde derivative of the olefin is also produced along with the pentenals. It has been found that the alkadiene reacts to form a complex with the metal more rapidly than certain of the olefins and requires more forcing conditions to be hydroformylated itself than certain of the olefins.

Mixtures of different olefinic starting materials can be employed, if desired, in the hydroformylation reactions. More preferably the hydroformylation reactions are especially useful for the production of pentenals, by hydroformylating alkadienes in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, n-propyl-7-octenoate, pentenals, e.g., 2-pentenal, 3-pentenal and 4-pentenal; penten-1-ols, e.g., 2-penten-1-ol, 3-penten-1-ol and 4-penten-1-ol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

As indicated above, it is generally preferred to carry out the hydroformylation process of this invention in a continuous manner. In general, continuous hydroformylation processes are well known in the art and may involve: (a) hydroformylating the olefinic or alkadiene starting material (s) with carbon monoxide and hydrogen in a liquid homogeneous reaction mixture comprising a solvent, the metal-ligand complex catalyst, and free ligand; (b) maintaining reaction temperature and pressure conditions favorable to the hydroformylation of the olefinic or alkadiene starting material(s); (c) supplying make-up quantities of the olefinic or alkadiene starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic or alkadiene starting material(s) and vaporized aldehyde product is removed from the liquid reaction mixture from whence the aldehyde product is recovered and make-up olefinic or alkadiene starting material(s), carbon monoxide and hydrogen are supplied to the liquid reaction medium for the next single pass through without recycling the unreacted olefinic or alkadiene starting material(s). However, it is generally desirable to employ a continuous process that involves either a liquid and/or gas recycle procedure. Such types of recycle procedure are well known in the art and may involve the liquid recycling of the metal-ligand complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

Illustrative substituted and unsubstituted pentenal intermediates that can be prepared by the processes of this invention include one or more of the following: cis-2-pentenal, trans-2-pentenal, cis-3-pentenal, trans-3-pentenal, and/or 4-pentenal, including mixtures of one or more of the above pentenals. Illustrative of suitable substituted and unsubstituted pentenals (including derivatives of pentenals) include those permissible substituted and unsubstituted pentenals which are described in Kirk-Othmer, Encyclopedia of Chemical Technology, Fourth Edition, 1996, the pertinent portions of which are incorporated herein by reference.

Illustrative substituted and unsubstituted 6-hydroxyhexanal intermediates that can be prepared by the processes of this invention include, for example, 6-hydroxyhexanal and substituted 6-hydroxyhexanals (e.g., 2-methyl-6-hydroxyhexanal and 3,4-dimethyl-6-hydroxyhexanal) and the like, including mixtures of one or more of the above 6-hydroxyhexanals. Illustrative of suitable substituted and unsubstituted 6-hydroxyhexanals (including derivatives of 6-hydroxyhexanals) include those permissible substituted and unsubstituted 6-hydroxyhexanals which are described in Kirk-Othmer, Encyclopedia of Chemical Technology, Fourth Edition, 1996, the pertinent portions of which are incorporated herein by reference.

As indicated above, the hydroformylation reactions may involve a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is common place to continuously or intermittently remove a portion of the liquid reaction product medium, containing, e.g., the aldehyde product, the solubilized metal-ligand complex catalyst, free ligand, and organic solvent, as well as byproducts produced in situ by the hydroformylation, e.g., aldehyde condensation byproducts etc., and unreacted olefinic or alkadiene starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains metal-ligand complex catalyst, solvent, free ligand and usually some undistilled aldehyde product is then recycled back, with or with out further treatment as desired, along with whatever by-product and non-volatilized gaseous reactants that might still also be dissolved in said recycled liquid residue, in any conventional manner desired, to the hydroformylation reactor, such as disclosed e.g., in the above-mentioned patents. Moreover the reactant gases so removed by such distillation from the vaporizer may also be recycled back to the reactor if desired.

In an embodiment of this invention, the aldehyde mixtures may be separated from the other components of the crude reaction mixtures in which the aldehyde mixtures are produced by any suitable method. Suitable separation methods include, for example, solvent extraction, crystallization, distillation, vaporization, phase separation, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference. The subsequent hydrogenation of the aldehyde mixtures may be conducted without the need to separate the aldehydes from the other components of the crude reaction mixtures.

As indicated above, at the conclusion of (or during) the process of this invention, the desired pentenals may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing pentenal product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction mixture may then be recycled back to the reactor as may, if desired, any other volatile materials, e.g., unreacted olefin or alkadiene, together with any hydrogen and carbon monoxide dissolved in the liquid reaction after separation thereof from the condensed pentenal product, e.g., by distillation in any conventional manner. It is generally desirable to employ an organophosphorus ligand whose molecular weight exceeds that of the higher boiling aldehyde oligomer byproduct corresponding to the pentenals or hydroxyhexanals being produced in the hydroformylation process. Another suitable recovery technique is solvent extraction or crystallization. In general, it is preferred to separate the desired pentenals or hydroxyhexanals from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product from the metal-ligand complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_5$ and $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

Particularly when conducting the process of this invention in a continuous liquid recycle mode employing an organophosphite ligand, undesirable acidic byproducts (e.g., a hydroxy alkyl phosphonic acid) may result due to reaction of the organophosphite ligand and the aldehydes over the course of the process. The formation of such byproducts undesirably lowers the concentration of the ligand. Such acids are often insoluble in the reaction mixture and such insolubility can lead to precipitation of an undesirable gelatinous byproduct and may also promote the autocatalytic formation of further acidic byproducts. The organopolyphosphite ligands used in the process of this invention have good stability against the formation of such acids. However, if this problem does occur, the liquid reaction effluent stream of a continuous liquid recycle process may be passed, prior to (or more preferably after) separation of the desired pentenal or hydroxyhexanal product therefrom, through any suitable weakly basic anion exchange resin, such as a bed of amine Amberlyst® resin, e.g., Amberlyst® A-21, and the like, to remove some or all of the undesirable acidic byproducts prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

The processes useful in this invention may involve improving the catalyst stability of any organic solubilized rhodium-organopolyphosphite complex catalyzed, liquid recycle hydroformylation process directed to producing aldehydes from olefinic unsaturated compounds which may experience deactivation of the catalyst due to recovery of the aldehyde product by vaporization separation from a reaction product solution containing the organic solubilized rhodium-organopolyphosphite complex catalyst and aldehyde product, the improvement comprising carrying out said vaporization separation in the presence of a heterocyclic nitrogen compound. See, for example, copending U.S. patent application Ser. No. 08/756,789, filed Nov. 26, 1996, the disclosure of which is incorporated herein by reference.

The processes useful in this invention may involve improving the hydrolytic stability of the organophosphite ligand and thus catalyst stability of any organic solubilized rhodium-organophosphite ligand complex catalyzed hydroformylation process directed to producing aldehydes from olefinic unsaturated compounds, the improvement comprising treating at least a portion of an organic solubilized rhodium-organophosphite ligand complex catalyst solution derived from said process and which also contains phosphorus acidic compounds formed during the hydroformylation process, with an aqueous buffer solution in order to neutralize and remove at least some amount of said phosphorus acidic compounds from said catalyst solution, and then returning the treated catalyst solution to the hydroformylation reactor. See, for example, copending U.S. patent application Ser. Nos. 08/756,501 and 08/753,505, both filed Nov. 26, 1996, the disclosures of which are incorporated herein by reference.

In an embodiment of this invention, deactivation of metal-organopolyphosphorus ligand complex catalysts caused by an inhibiting or poisoning organomonophosphorus compound can be reversed or at least minimized by carrying out hydroformylation processes in a reaction region where the hydroformylation reaction rate is of a negative or inverse order in carbon monoxide and optionally at one or more of the following conditions: at a temperature such that the temperature difference between reaction product fluid temperature and inlet coolant temperature is sufficient to prevent and/or lessen cycling of carbon monoxide partial pressure, hydrogen partial pressure, total reaction pressure, hydroformylation reaction rate and/or temperature during said hydroformylation process; at a carbon monoxide conversion sufficient to prevent and/or lessen cycling of carbon monoxide partial pressure, hydrogen partial pressure, total reaction pressure, hydroformylation reaction rate and/or temperature during said hydroformylation process; at a hydrogen conversion sufficient to prevent and/or lessen cycling of carbon monoxide partial pressure, hydrogen partial pressure, total reaction pressure, hydroformylation reaction rate and/or temperature during said hydroformylation process; and at an olefinic unsaturated compound conversion sufficient to prevent and/or lessen cycling of carbon monoxide partial pressure, hydrogen partial pressure, total reaction pressure, hydroformylation reaction rate and/or temperature during said hydroformylation process. See, for example, copending U.S. patent application Ser. No. 08/756, 499, filed Nov. 26, 1996, the disclosure of which is incorporated herein by reference.

Hydrogenation Steps or Stages

The hydrogenation processes may involve: (a) converting one or more substituted or unsubstituted pentenals to one or more substituted or unsubstituted penten-1-ols; (b) converting one or more substituted or unsubstituted 6-hydroxyhexanals to one or more substituted or unsubstituted 1,6-hexanediols; and (c) converting one or more substituted or unsubstituted 1,6-hexanedials to one or more substituted or unsubstituted 6-hydroxyhexanals and/or 1,6-hexanediols. In general, the hydrogenation step or stage comprises reacting one or more substituted or unsubstituted pentenals with hydrogen in the presence of a catalyst to produce one or more substituted or unsubstituted penten-1-ols, reacting one or more substituted or unsubstituted 6-hydroxyhexanals with hydrogen in the presence of a catalyst to produce one or more substituted or unsubstituted 1,6-hexanediols, and reacting one or more substituted or unsubstituted 1,6-hexanedials with hydrogen in the presence of a catalyst to produce one or more substituted or unsubstituted 6-hydroxyhexanals and/or 1,6-hexanediols.

Illustrative of suitable hydrogenation processes are described, for example, in U.S. Pat. Nos. 5,004,845, 5,003, 110, 4,762,817 and 4,876,402, the disclosures of which are incorporated herein by reference. As used herein, the term "hydrogenation" is contemplated to include, but is not limited to, all permissible hydrogenation processes including those involved with reductive hydroformylation and shall include, but are not limited to, the following: (a) converting one or more substituted or unsubstituted pentenals to one or more substituted or unsubstituted penten-1-ols; (b) converting one or more substituted or unsubstituted 6-hydroxyhexanals to one or more substituted or unsubstituted 1,6-hexanediols; and (c) converting one or more substituted or unsubstituted 1,6-hexanedials to one or more substituted or unsubstituted 6-hydroxyhexanals and/or 1,6-hexanediols.

Pentenals, 6-hydroxyhexanals and 1,6-hexanedials useful in the hydrogenation process are known materials and can be prepared by the hydroformylation and/or hydrogenation steps described above or by conventional methods. Reaction mixtures comprising pentenals, 6-hydroxyhexanals and 1,6-hexanedials may be useful herein. The amount of pentenals, 6-hydroxyhexanals and 1,6-hexanedials employed in the hydrogenation step is not narrowly critical and can be any amount sufficient to produce penten-1-ols and 1,6-hexanediols respectively, preferably in high selectivities.

The reactors and reaction conditions for the hydrogenation reaction step are known in the art. The particular hydrogenation reaction conditions are not narrowly critical and can be any effective hydrogenation conditions sufficient to produce one or more penten-1-ols and 1,6-hexanediols. The reactors may be stirred tanks, tubular reactors and the like. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions. Recovery and purification may be by any appropriate means, and may include distillation, phase separation, extraction, absorption, crystallization, membrane, derivative formation and the like.

The particular hydrogenation reaction conditions are not narrowly critical and can be any effective hydrogenation procedures sufficient to produce one or more penten-1-ols and 1,6-hexanediols. The combination of relatively low temperatures and low hydrogen pressures as described below may provide good reaction rates and high product selectivities. The hydrogenation reaction may proceed in the presence of water without substantial degradation of the hydrogenation catalyst.

The hydrogenation reaction can be conducted at a temperature of from about 0C. ° to 180° C. for a period of about 1 hour or less to about 12 hours or longer with the longer time being used at the lower temperature, preferably from about 25° C. to about 140° C. for about 1 hour or less to about 8 hours or longer, and more preferably at about 50° C. to 125° C. for about 1 hour or less to about 3 hours or longer.

The hydrogenation reaction can be conducted over a wide range of hydrogen pressures ranging from about 50 psig to about 10000 psig, preferably from about 200 psig to about 1500 psig. It is most preferable to conduct the hydrogenation reaction at hydrogen pressures of from about 500 psig to about 1000 psig. The reaction is preferably effected in the liquid or vapor states or mixtures thereof, more preferably in the liquid state.

Transfer hydrogenation may be used to hydrogenate an aldehyde to an alcohol. In this process, the hydrogen required for the reduction of the aldehyde is obtained by dehydrogenation of an alcohol to an aldehyde or ketone. Transfer hydrogenation can be catalyzed by a variety of catalysts, both homogeneous or heterogeneous. For example, a common catalyst is aluminum isopropoxide and a common alcohol is isopropanol. This system has the advantage that the resultant ketone, acetone, is volatile and can be easily removed from the reaction system by vaporization. Since transfer hydrogenation is generally an equilibrium limited process, removal of a volatile product can be used to drive the reaction to completion. The acetone produced in such a process may be hydrogenated in a separate step and recycled to the transfer hydrogenation reaction if desired. Other suitable catalysts for the transfer hydrogenation reaction include those known heterogeneous hydrogenation and dehydrogenation catalysts described below. Useful homogeneous catalysts include, for example, aluminum alkoxides and halides, zirconium, ruthenium and rhodium.

The hydrogenation reaction can be conducted using known hydrogenation catalysts in conventional amounts. Illustrative of suitable hydrogenation catalysts include, for example, Raney-type compounds such as Raney nickel and modified Raney nickels; molybdenum-promoted nickel, chromium-promoted nickel, cobalt-promoted nickel; platinum; palladium; iron; cobalt molybdate on alumina; copper chromite; barium promoted copper chromite; tin-copper couple; zinc-copper couple; aluminum-cobalt; aluminum-copper; aluminum-nickel; platinum; nickel; cobalt; ruthenium; rhodium; iridium; palladium; rhenium; copper; yttrium on magnesia; lanthanide metals such as lanthanum and cerium; platinum/zinc/iron; platinum/cobalt; Raney cobalt; osmium; and the like. The preferred catalysts are nickel, platinum, cobalt, rhenium and palladium. The hydroformylation and hydrogenation reaction conditions may be the same or different and the hydroformylation and hydrogenation catalysts may be the same or different. Suitable catalysts useful in both the hydroformylation and hydrogenation reactions include, for example, ligand-free rhodium, phosphine-promoted rhodium, amine-promoted rhodium, cobalt, phosphine-promoted cobalt, ruthenium, and phosphine-promoted palladium catalysts. Mixtures of hydrogenation catalysts and hydroformylation catalysts described above may be employed if desired. As indicated above, the hydrogenation catalyst may be homogeneous or heterogeneous.

The amount of catalyst used in the hydrogenation reaction is dependent on the particular catalyst employed and can range from about 0.01 weight percent or less to about 10 weight percent or greater of the total weight of the starting materials.

Illustrative substituted and unsubstituted penten-1-ol intermediates that can be prepared by the processes of this invention include one or more of the following: cis-2-penten-1-ol, trans-2-penten-1-ol, cis-3-penten-1-ol, trans-3-penten-1-ol, and/or 4-penten-1-ol, including mixtures comprising one or more of the above penten-1-ols. Illustrative of suitable substituted and unsubstituted penten-1-ols (including derivatives of penten-1-ols) include those permissible substituted and unsubstituted penten-1-ols which are described in Kirk-Othmer, Encyclopedia of Chemical Technology, Fourth Edition, 1996, the pertinent portions of which are incorporated herein by reference.

Illustrative substituted and unsubstituted 1,6-hexanediols that can be prepared by the processes of this invention include 1,6-hexanediol and substituted 1,6-hexanediols (e.g., 2-methyl-1,6-hexanediol and 3,4-dimethyl-1,6-hexanediol) and the like. Illustrative of suitable substituted and unsubstituted 1,6-hexanediols (including derivatives of 1,6-hexanediols) include those permissible substituted and unsubstituted 1,6-hexanediols which are described in Kirk-Othmer, Encyclopedia of Chemical Technology, Fourth Edition, 1996, the pertinent portions of which are incorporated herein by reference.

As indicated above, the substituted and unsubstituted penten-1-ols and 1,6-hexanediols produced by the hydrogenation step of this invention can be separated by conventional techniques such as distillation, extraction, precipitation, crystallization, membrane separation, phase separation or other suitable means. For example, a crude reaction product can be subjected to a distillation-separation at atmospheric or reduced pressure through a packed distillation column. Reactive distillation may be useful in conducting the hydrogenation reaction step.

A one-step process involving the reductive hydroformylation of one or more substituted or unsubstituted alkadienes to produce one or more substituted or unsubstituted 1,6-hexanediols is disclosed in copending U.S. patent application Ser. No. 60/016,287, filed Apr. 24, 1996, the disclosure of which is incorporated herein by reference. Another process involving the hydrocarbonylation of one or more substituted or unsubstituted alkadienes or penten-1-ols to produce one or more substituted or unsubstituted 1,6-hexanediols is disclosed in copending U.S. patent application Ser. No. 08/843-336, filed on an even date herewith, the disclosure of which is incorporated herein by reference.

An embodiment of this invention relates to a process for producing one or more substituted or unsubstituted 1,6-hexanediols which comprises:

(a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or carbon monoxide partial pressure sufficient to selectively produce one or more substituted or unsubstituted unsaturated aldehydes comprising 3-pentenals, 4-pentenal and/or 2-pentenals;

(b) optionally separating the 3-pentenals, 4-pentenal and/or 2-pentenals from the hydroformylation catalyst;

(c) subjecting said one or more substituted or unsubstituted unsaturated aldehydes comprising 3-pentenals, 4-pentenal and/or 2-pentenals to hydrogenation in the presence of a hydrogenation catalyst to produce one or more substituted or unsubstituted unsaturated alcohols comprising 3-penten-1-ols, 4-penten-1-ol and/or 2-penten-1-ols;

(d) optionally separating the 3-penten-1-ols, 4-penten-1-ol and/or 2-penten-1-ols from the hydrogenation catalyst; and (e) subjecting said one or more substituted or unsubstituted unsaturated alcohols comprising 3-penten-1-ols, 4-penten-1-ol and/or 2-penten-1-ols to reductive hydroformylation in the presence of a reductive hydroformylation catalyst, e.g., a metal-organophosphorus ligand complex catalyst, to produce one or more substituted or unsubstituted 1,6-hexanediols. The reaction conditions in steps (a) and (e) may be the same or different and the hydroformylation catalyst in step (a) and the reductive hydroformylation catalyst in step (e) may be the same or different.

Yet another embodiment of this invention relates to a process for producing one or more substituted or unsubstituted 1,6-hexanediols which comprises:

(a) subjecting one or more substituted or unsubstituted alkadienes, e.g., butadiene, to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted unsaturated aldehydes comprising 3-pentenals, 4-pentenal and/or 2-pentenals;

(b) optionally separating the 3-pentenals, 4-pentenal and/or 2-pentenals from the hydroformylation catalyst;

(c) optionally subjecting the 2-pentenals and/or 3-pentenals to isomerization in the presence of a heterogeneous or homogeneous olefin isomerization catalyst to partially or completely isomerize the 2-pentenals and/or 3-pentenals to 3-pentenals and/or 4-pentenal;

(d) subjecting said one or more substituted or unsubstituted unsaturated aldehydes comprising 3-pentenals, 4-pentenal and/or 2-pentenals to hydrogenation in the presence of a hydrogenation catalyst to produce one or more substituted or unsubstituted unsaturated alcohols comprising 3-penten-1-ols, 4-penten-1-ol and/or 2-penten-1-ols;

(e) optionally separating the 3-penten-1-ols, 4-penten-1-ol and/or 2-penten-1-ols from the hydrogenation catalyst; and (f) subjecting said one or more substituted or unsubstituted unsaturated alcohols comprising 2-penten-1-ols, 3-penten-1-ols and/or 4-penten-1-ol to reductive hydroformylation in the presence of a reductive hydroformylation catalyst, e.g., a metal-organophosphorus ligand complex catalyst, to produce one or more substituted or unsubstituted 1,6-hexanediols. The reaction conditions in steps (a) and (f) may be the same or different and the hydroformylation catalyst in step (a) and the reductive hydroformylation catalyst in step (f) may be the same or different. In an embodiment, step (d) may optionally include subjecting the 2-penten-1-ols and/or 3-penten-1-ols to isomerization in the presence of a heterogeneous or homogeneous olefin isomerization catalyst to partially or completely isomerize the 2-penten-1-ols and/or 3-penten-1-ols to 3-penten-1-ols and/or 4-penten-1-ol.

The olefin isomerization catalyst in step (c) and optionally step (d) may be any of a variety of homogeneous or heterogeneous transition metal-based catalysts (particularly Ni, Rh, Pd, Pt, Co, Ru, or Ir), or may be a heterogeneous or homogeneous acid catalyst (particularly any acidic zeolite, polymeric resin, or source of $H^+$, any of which may be modified with one or more transition metals). Such olefin isomerization catalysts are known in the art and the isomerization can be conducted by conventional procedures known in the art. As used herein, the term "isomerization" is contemplated to include, but is not limited to, all permissible isomerization processes which involve (a) converting one or more substituted or unsubstituted 2-pentenals and/or 3-pentenals to one or more substituted or unsubstituted 4-pentenals, and (b) converting one or more substituted or unsubstituted 2-penten-1-ols and/or 3-penten-1-ols to one or more substituted or unsubstituted 4-penten-1-ols.

When the processes of this invention are conducted in three stages (i.e., first producing 2-pentenals, 3-pentenals and/or 4-pentenal under one set of conditions and then producing 2-penten-1-ols, 3-penten-1-ols and/or 4-penten-1-ol under another set of conditions and then producing a 1,6-hexanediol from the 2-penten-1-ols, 3-penten-1-ols and/or 4-penten-1-ol (or the acetals) under another set of conditions), it is preferred to conduct the first stage at a temperature from 75° C. to 110° C. and at a total pressure from 250 psi to 1000 psi, the second stage at a temperature from about 25° C. to 200° C. and at a pressure from about 15 psi to 2000 psi and to conduct the third stage at a temperature from 60° C. to 100° C. and at a pressure from 100 psi to 500 psi. The same or different catalysts can be used in the first and third stages. The other conditions can be the same or different in all three stages.

The 1,6-hexanediols products have a wide range of utilities that are well known in the art, e.g., they are useful as starting materials/intermediates in the production of polyesters. The 1,6-hexanediols may also be useful as starting materials/intermediates in the production of caprolactones and caprolactams.

Cyclization Step

The cyclization process involves converting one or more substituted or unsubstituted 1,6-hexanediols, e.g., a 1,6-hexanediol, or a reaction mixture comprising one or more substituted or unsubstituted 1,6-hexanediols to one or more substituted or unsubstituted epsilon caprolactones or a reaction mixture comprising one or more substituted or unsubstituted epsilon caprolactones. As used herein, the term "cyclization" is contemplated to include all permissible cyclization processes which involve converting one or more substituted or unsubstituted 1,6-hexanediols, e.g., 1,6-hexanediol, or a reaction mixture comprising one or more substituted or unsubstituted 1,6-hexanediols to one or more substituted or unsubstituted epsilon caprolactones or a reaction mixture comprising one or more substituted or unsubstituted epsilon caprolactones. As used herein, the term "epsilon caprolactone" is contemplated to include all permissible substituted or unsubstituted epsilon caprolactones which may be derived from one or more substituted or unsubstituted 1,6-hexanediols, e.g., 1,6-hexanediol, or a reaction mixture comprising one or more substituted or unsubstituted 1,6-hexanediols.

Illustrative of substituted or unsubstituted 1,6-hexanediols include, for example, 1,6-hexanediol or its acetals, and the like. 1,6-Hexanediols useful in the cyclization process are known materials and can be prepared by conventional methods. For example, 1,6-hexanediol can be produced by the hydroformylation and hydrogenation steps described above or by other conventional processes. Reaction mixtures comprising 1,6-hexanediols may be useful herein. The amount of 1,6-hexanediols employed in the cyclization step is not narrowly critical and can be any amount sufficient to produce epsilon caprolactone, preferably in high selectivities.

The particular cyclization reaction conditions are not narrowly critical and can be any effective cyclization procedures sufficient to produce the epsilon caprolactone.

The cyclization reaction can be conducted at a temperature of from about 50° C. to about 400° C. for a period of about 1 hour or less to about 4 hours or longer with the longer time being used at the lower temperature, preferably from about 100° C. to about 350° C. for about 1 hour or less to about 2 hours or longer, and more preferably at about 150° C. to about 300° C. for about 1 hour or less.

The cyclization reaction can be conducted over a wide range of pressures ranging from about 15 psig to about 2000 psig. It is preferable to conduct the cyclization reaction at pressures of from about 15 psig to about 1000 psig. The cyclization reaction is preferably effected in the liquid or vapor states or mixtures thereof.

The cyclization reaction can be conducted using known catalysts in conventional amounts. Illustrative of suitable cyclization catalysts include, for example, barium promoted copper chromite, chromium promoted with barium, manganese, copper, calcium, zinc, for example, barium promoted copper chromite, silver on alumina, molybdenum oxide on alumina, copper/zinc oxides either supported on alumina or bulk oxides, platinum/tin on alumina, copper/chromium/barium, cobalt on alumina/silica. Preferred cyclization catalysts include barium promoted copper chromite, and copper/zinc oxide on alumina, and the like. The specific catalyst used should be capable of transforming 1,6-hexanediol to epsilon caprolactone in high yield under mild conditions. The catalyst may be homogeneous or heterogeneous. Appropriate ligands or promoters may be incorporated into such catalysts to modify catalyst activity, selectivity, lifetime or ease of operability. Such ligands and promoters are known materials and can be used in conventional amounts.

The amount of cyclization catalyst used is dependent on the particular cyclization catalyst employed and can range from about 0.01 weight percent or less to about 10 weight percent or greater of the total weight of the starting materials.

Such cyclization reactions may be performed in any appropriate solvent, under any appropriate atmosphere, or in the gas phase. Such solvents and atmospheres are chosen to allow the most desirable catalyst performance. For example, reactions may be performed under hydrogen gas in order to stabilize the catalyst from decomposition reactions to unproductive catalysts. Suitable solvents include ethers, esters, lactones (such as epsilon caprolactone), ketones, aliphatic or aromatic hydrocarbons, fluorocarbons, silicones, polyethers, chlorinated hydrocarbons and the like.

The epsilon caprolactone produced by the cyclization step of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the cyclization reaction step.

Illustrative epsilon caprolactones that can be prepared by the processes of this invention include epsilon caprolactone and substituted epsilon caprolactones (e.g., alpha, beta, gamma and delta substituted epsilon caprolactones). Illustrative of suitable substituted and unsubstituted epsilon caprolactones (including derivatives of epsilon caprolactones) include those permissible substituted and unsubstituted epsilon caprolactones described in Kirk-Othmer, Encyclopedia of Chemical Technology, Third Edition, 1984, the pertinent portions of which are incorporated herein by reference.

The substituted or unsubstituted epsilon caprolactone products have a wide range of utilities that are well known in the art, e.g., they are useful as starting materials/intermediates in the production of epsilon caprolactam and polyesters.

The processes of this invention can be operated over a wide range of reaction rates (m/L/h=moles of product/liter of reaction solution/hour). Typically, the reaction rates are at least 0.01 m/L/h or higher, preferably at least 0.1 m/L/h or higher, and more preferably at least 0.5 m/L/h or higher. Higher reaction rates are generally preferred from an economic standpoint, e.g., smaller reactor size, etc.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes useful in this invention may be carried out in a multistaged reactor such as described, for example, in copending U.S. patent application Ser. No. 08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The substituted and unsubstituted 1,6-hexanediols produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, copolymerization, condensation polymerization, etherification, amination, alkylation, dehydrogenation, reduction, acylation, cyclization, dehydration, condensation, carboxylation, carbonylation, oxidation, silylation and the like, including permissible combinations thereof. Preferred derivatization reactions and derivatives of 1,6-hexanediols include, for example, amination to give hexamethylenediamine, oxidation to give adipic acid, oxidation and cyclization to give epsilon caprolactone, and oxidation, cyclization and amination to give epsilon caprolactam. This invention is not intended to be limited in any manner by the permissible derivatization reactions or permissible derivatives of substituted and unsubstituted 1,6-hexanediols.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLES 1–19

Into a 100 milliliter overhead stirred high pressure reactor was charged 0.25 mmol of dicarbonylacetylacetonato rhodium (I), 0.9 mmol of a trialkylphosphine defined in Table A below, 3 milliliters of butadiene, 26 milliliters of a solvent as defined in Table A, and 1 milliliter of diglyme as internal standard. The reactor was pressurized with 5–10 psi of hydrogen/carbon monoxide in 1/1 ratio and heated to the desired temperature set out in Table A. At the desired temperature, the reactor was pressurized to the desired hydrogen/carbon monoxide ratio set out in Table A and the gas uptake was monitored. After a decrease in pressure of 10%, the reactor was re-pressurized to the initial value with hydrogen/carbon monoxide in 1/1 ratio. Samples of the reaction mixture were taken in dry ice cooled vials via the sampling line at scheduled intervals and analyzed by gas chromatography. At the end of the reaction period of 90 minutes, the gases were vented and the reaction mixture drained. Further details and results of analyses are set out in Table A.

TABLE A

| Ex. No. | Solvent/Promoter | Phosphine | Temp. (° C.) | $H_2$/CO (psi) | Butadiene Conv. (%) | Rate m/L/h | Selectivity (%) 3 & 4 Pentenols |
|---|---|---|---|---|---|---|---|
| 1 | Ethanol | Triethylphosphine | 60 | 300/300 | 27 | 0.2 | 92 |
| 2 | Ethanol | Triethylphosphine | 80 | 300/300 | 90 | 1.6 | 87 |
| 3 | Ethanol | Triethylphosphine | 80 | 500/500 | 87 | 1.3 | 91 |
| 4 | Ethanol | Triethylphosphine | 80 | 75/75 | 75 | 0.3 | 71 |
| 5 | Octanol | Trioctylphosphine | 80 | 600/200 | 98 | 1.9 | 88 |
| 6 | 3-Pentenol | Trioctylphosphine | 80 | 600/200 | 89 | nd | 90 |
| 7 | Hexanediol | Trioctylphosphine | 80 | 300/300 | 65 | nd | 93 |
| 8 | Pyrrole | Trioctylphosphine | 80 | 600/200 | 90 | 1.4 | 88 |
| 9 | Ethanol | Tributylphosphine | 80 | 300/300 | 55 | 1.0 | 70 |
| 10 | Phenol/THF | Trioctylphosphine | 80 | 600/200 | 84 | 2.0 | 55 |
| 11 | t-Butanol | Triethylphosphine | 120 | 250/250 | 99 | nd | 38 (15 min rxn. time) |
| 12 | Ethanol | Trimethylphosphine | 120 | 250/250 | 97 | nd | 42 (2 h rxn. time) |
| 13 | Ethanol | Diethyl-para-N,N-dimethylphenylphosphine | 80 | 600/200 | 70 | 1.2 | 64 |
| 14 | Ethanol/Acetonitrile | Triethylphosphine | 80 | 300/300 | 68 | 1.1 | 82 |
| 15 | Ethanol/Tetraglyme | Triethylphosphine | 80 | 300/300 | 64 | 1.0 | 91 |
| 16 | Diphenylamine | Trioctylphosphine | 80 | 600/200 | 80 | 0.8 | 54 |
| 17 | Acetamide | Trioctylphosphine | 80 | 600/200 | 85 | 0.9 | 34 |
| 18 | Methylacetamide | Trioctylphosphine | 80 | 600/200 | 73 | 0.8 | 59 |
| 19 | N-Methylformamide | Trioctylphosphine | 80 | 600/200 | 33 | 0.9 | 19 | nd = not determined

EXAMPLES 20–26

Into a 100 milliliter overhead stirred high pressure reactor was charged 0.25 mmol of dicarbonylacetylacetonato rhodium (I), 0.9 mmol of a trialkylphosphine defined in Table B below, 3 milliliters of butadiene, 26 milliliters of ethanol, and 1 milliliter of diglyme as internal standard. The reactor was pressurized with 5–10 psi of hydrogen/carbon monoxide in 1/1 ratio and heated to 80° C. At the desired temperature, the reactor was pressurized to the desired hydrogen/carbon monoxide ratio set out in Table B and the gas uptake was monitored. After a decrease in pressure of 10%, the reactor was re-pressurized to the initial value with hydrogen/carbon monoxide in 1/1 ratio. Samples of the reaction mixture were taken in dry ice cooled vials via the sampling line at scheduled intervals and analyzed by gas chromatography. At the end of the reaction period of 120 minutes, the gases were vented and the reaction mixture drained. Further details and results of analyses are set out in Table B.

TABLE B

| Ex. No. | Phosphine | $H_2$/CO (psi) | Butadiene Conv. (%) | Rate (m/L/h) | Selectivity (%) 3 & 4 Pentenols |
|---|---|---|---|---|---|
| 20 | t-butyldiethyl phosphine | 300/300 | 60 | 0.8 | 13 |
| 21 | t-butyldiethyl phosphine | 800/200 | 69 | 1.1 | 19 |
| 22 | cyclohexyldiethyl phosphine | 300/300 | 76 | 0.7 | 75 |
| 23 | cyclohexyldiethyl phosphine | 800/200 | 82 | 1.4 | 80 |
| 24 | n-butyldiethyl phosphine | 300/300 | 77 | 1.1 | 82 |
| 25 | diethylphenyl phosphine | 200/800 | 53 | 0.9 | 77 |
| 26 | ethyldiphenyl phosphine | 200/800 | 38 | 0.6 | 27 |

EXAMPLE 27

A 160 milliliter magnetically stirred autoclave was purged with 1:1 $H_2$/CO and charged with a catalyst solution consisting of 0.1125 grams (0.44 mmol) dicarbonylacetylacetonato rhodium (I), 0.3515 grams (2.94 mmol) P($CH_2CH_2CH_2OH$)$_3$, and 44.1 grams tetrahydrofuran. The autoclave was pressurized with 40 psig 1:1 $H_2$/CO and heated to 80° C. 6 milliliters (3.73 grams) of 1,3-butadiene was charged with a metering pump and the reactor was pressurized to 1000 psig with 1:1 $H_2$/CO. The reaction mixture was maintained at 80° C. under 1000 psi 1:1 $H_2$/CO. Samples of the reaction mixture taken after 90 minutes and 170 minutes provided the results set out in Table C below.

TABLE C

| Time (minutes) | Temperature (° C.) | $H_2$/CO (psig) | Butadiene Conversion (%) | Rate (m/L/h) | Selectivity (%) 3 & 4 Pentenols |
|---|---|---|---|---|---|
| 90 | 80 | 500/500 | 81 | 0.7 | 66 |
| 170 | 80 | 500/500 | 96 | 0.4 | 72 |

EXAMPLE 28

A 160 milliliter magnetically stirred autoclave was purged with 1:1 $H_2$/CO and charged with a catalyst solution consisting of 0.1126 grams (0.44 mmol) dicarbonylacetylacetonato rhodium (I), 0.6120 grams (1.69 mmol) P($CH_2CH_2CH_2OH$)$_3$, and 39.9 grams of ethanol. The autoclave was pressurized with 40 psig 1:1 $H_2$/CO and heated to 80° C. 6 milliliters (3.73 grams) of 1,3-butadiene was charged with a metering pump and the reactor pressurized to 1000 psig with 1:1 $H_2$/CO. The reaction mixture was maintained at 80° C. under 1000 psi 1:1 $H_2$/CO. Samples of the reaction mixture taken after 15 and 43 minutes provided the results set out in Table D below.

TABLE D

| Time (minutes) | Temperature (° C.) | $H_2$/CO (psig) | Butadiene Conversion (%) | Rate (m/L/h) | Selectivity (%) 3 & 4 Pentenols |
|---|---|---|---|---|---|
| 15 | 80 | 500/500 | 53 | 2.6 | 70 |
| 43 | 80 | 500/500 | 89 | 1.5 | 78 |

EXAMPLE 29

A 160 milliliter magnetically stirred autoclave was purged with 1:1 $H_2$/CO and charged with a catalyst solution consisting of 0.1125 grams (0.44 mmol) of dicarbonylacetylacetonato rhodium (I), 0.3515 grams (2.94 mmol) of P($CH_2CH_2CH_2OH$)$_3$, and 44.1 grams of tetrahydrofuran. The autoclave was pressurized with 40 psig 1:1 $H_2$/CO and heated to 80° C. 6 milliliters (3.73 grams) of 1,3-butadiene was charged with a metering pump and the reactor pressurized to 1000 psig with 1:1 $H_2$/CO. The reaction mixture was maintained at 80° C. under 1000 psi 1:1 $H_2$/CO. A sample of the reaction mixture taken after 90 minutes provided the results set out in Table E below.

TABLE E

| Time (minutes) | Temperature (° C.) | $H_2$/CO (psig) | Butadiene Conversion (%) | Rate (m/L/h) | Selectivity (%) 3 & 4 Pentenols |
|---|---|---|---|---|---|
| 90 | 80 | 500/500 | 81 | 0.7 | 2 |

EXAMPLE 30

A 160 milliliter magnetically stirred autoclave was purged with 1:1 $H_2$/CO and charged with a catalyst solution consisting of 0.1126 grams (0.44 mmol) of dicarbonylacetylacetonato rhodium (I), 0.6120 grams (1.69 mmol) of P($CH_2CH_2CH_2OH$)$_3$, and 39.9 grams of ethanol. The autoclave was pressurized with 40 psig 1:1 $H_2$/CO and heated to 80° C. 6 milliliters (3.73 grams) of 1,3-butadiene was charged with a metering pump and the reactor pressurized to 1000 psig with 1:1 $H_2$/CO. The reaction mixture was maintained at 80° C. under 1000 psi 1:1 $H_2$CO. A sample of the reaction mixture taken after 60 minutes provided the results set out in Table F below.

TABLE F

| Time (minutes) | Temperature (° C.) | $H_2$/CO (psig) | Butadiene Conversion (%) | Rate (m/L/h) | Selectivity (%) 3 & 4 Pentenols |
|---|---|---|---|---|---|
| 60 | 80 | 500/500 | 89 | 1.1 | 4 |

EXAMPLES 31–34

A 100 milliliter overhead stirred high pressure reactor was charged with 0.25 mmol of dicarbonylacetylacetonato rhodium (I), 0.9 mmol of a trialkylphosphine (as defined in Table G below), 3 milliliters of butadiene, 26 milliliters of ethanol, and 1 milliliter of digylme as internal standard. The reactor was pressurized with 5–10 psi of hydrogen/carbon monoxide in 1/1 ratio and heated to 80° C. At the desired temperature, the reactor was pressurized to the desired hydrogen/carbon monoxide ratio set out in Table G and the gas uptake was monitored. After a 10% drop in the reactor pressure, the reactor was re-pressurized to the initial value with hydrogen/carbon monoxide in 1/1 ratio. At the end of the reaction period of 120 minutes, the gases were vented and the reaction mixture drained and analyzed by gas chromatography. Further details and results of analyses are set out in Table G.

TABLE H

| Example | [Rh] (ppm) | [Co] (ppm) | PEt$_3$ (mmol) | Butadiene (mmols) | Temp (° C.) | P(CO) (psig) | P(H$_2$) (psig) | Time (min) |
|---|---|---|---|---|---|---|---|---|
| 35 | 309 | 315 | 0.3 | 34.8 | 100 | 250 | 400 | 113 |
| 36 | 604 | 313 | 1.0 | 36.7 | 125 | 550 | 600 | 120 |
| 37 | 911 | 311 | 1.6 | 33.8 | 150 | 400 | 800 | 148 |
| 38 | 965 | 654 | 1.0 | 33.3 | 100 | 400 | 600 | 124 |
| 39 | 297 | 599 | 2.1 | 33.1 | 125 | 250 | 800 | 110 |
| 40 | 594 | 593 | 0.3 | 36.9 | 150 | 400 | 550 | 138 |
| 41 | 300 | 892 | 2.1 | 27.6 | 100 | 550 | 600 | 115 |
| 42 | 606 | 892 | 0.3 | 34.2 | 150 | 400 | 800 | 138 |
| 43 | 900 | 900 | 1.1 | 33.7 | 150 | 250 | 400 | 120 |
| 44 | 600 | 300 | 1.7 | 67.0 | 100 | 400 | 400 | 121 |
| 45 | 916 | 312 | 0.3 | 68.1 | 125 | 250 | 600 | 99 |
| 46 | 330 | 332 | 1.0 | 31.5 | 150 | 550 | 800 | 122 |
| 47 | 911 | 597 | 0.3 | 66.7 | 100 | 550 | 800 | 120 |
| 48 | 307 | 586 | 1.2 | 66.7 | 125 | 400 | 400 | 138 |
| 49 | 600 | 600 | 1.9 | 69.6 | 150 | 250 | 600 | 112 |
| 50 | 601 | 910 | 1.2 | 68.6 | 100 | 250 | 800 | 138 |
| 51 | 885 | 874 | 1.9 | 69.5 | 150 | 400 | 600 | 138 |
| 52 | 324 | 789 | 0.4 | 71.9 | 150 | 400 | 600 | 120 |

TABLE G

| Ex. No. | Trialkylphosphine | H$_2$/CO (psi) | Butadiene Conv. (%) | Rate (m/L/h) | Selectivity to 1,6-hexanediol (%) |
|---|---|---|---|---|---|
| 31 | cyclohexyl-diethylphosphine | 300/300 | 76 | 0.7 | 7.2 |
| 32 | cyclohexyl-diethylphosphine | 800/200 | 82 | 1.4 | 7.2 |
| 33 | n-butyldiethyl-phosphine | 300/300 | 77 | 1.1 | 5.9 |
| 34 | diethylphenyl-phosphine | 200/800 | 53 | 0.9 | 3.0 |

EXAMPLES 35–52

Catalysts were prepared by mixing dicarbonylacetylacetonato rhodium (I), [Co$_2$(CO)$_8$] and ethanol (30 milliliters) in a Schlenk flask under nitrogen such that the individual metal concentrations of Table H were achieved. Triethylphosphine (amount indicated in Table H) was added as a 1.0 molar solution in tetrahydrofuran along with a measured quantity of diglyme as internal standard. The mixture was stirred for 5–10 minutes before being transferred to a 100 milliliter stainless steel Parr autoclave. The desired quantity of butadiene was then added by syringe. The bomb was then pressurized with about 25% of the desired final pressure of carbon monoxide and about 25% of the desired final hydrogen partial pressure before being heated to the final desired reaction temperature, when carbon monoxide and hydrogen were added in an amount to achieve the desired final partial pressures (all indicated in Table H). The reaction was allowed to proceed for the indicated length of time. When the total pressure had dropped to 90% of the desired total pressure, 2:1 synthesis gas (a mixture of hydrogen and carbon monoxide) was added to raise the total pressure back to 100% of that desired. The reactor was cooled to ambient temperature and vented to atmospheric pressure and the contents analyzed by gas chromatography to give the results indicated in Table I.

TABLE I

| Example | Penten-1-als | Penten-1-ols | 6-Hydroxy-hexanal | 1,6-Hexanediol |
|---|---|---|---|---|
| 35 | 1.7 | 68.7 | 2.0 | 3.7 |
| 36 | 0.0 | 29.4 | 0.0 | 8.7 |
| 37 | 3.8 | 3.3 | 0.0 | 0.0 |
| 38 | 0.0 | 79.3 | 0.0 | 7.5 |
| 39 | 0.0 | 62.5 | 0.9 | 8.5 |
| 40 | 4.6 | 0.0 | 1.6 | 2.4 |
| 41 | 2.5 | 13.0 | 0.0 | 0.0 |
| 42 | 6.1 | 0.0 | 1.8 | 0.0 |
| 43 | 0.0 | 0.0 | 0.0 | 9.8 |
| 44 | 0.0 | 74.8 | 0.7 | 5.2 |
| 45 | 1.9 | 0.0 | 2.5 | 1.0 |
| 46 | 0.0 | 4.4 | 0.6 | 10.2 |
| 47 | 0.0 | 42.0 | 0.6 | 7.8 |
| 48 | 0.0 | 53.1 | 1.0 | 7.3 |
| 49 | 0.0 | 1.3 | 0.4 | 9.5 |
| 50 | 0.4 | 79.2 | 0.9 | 5.4 |
| 51 | 0.0 | 54.8 | 0.6 | 8.5 |
| 52 | 5.8 | 1.0 | 0.0 | 0.0 |

EXAMPLES 53–60

Catalysts were prepared by mixing dicarbonylacetylacetonato rhodium (I) (0.11 mmols), PEt3 (1.0 molar in tetrahydrofuran) and PhP(CH$_2$CN)$_2$, diglyme (gas chromatograph internal standard: 1 milliliter) and ethanol (23 milliliters) in a Schlenk flask under nitrogen such that the ligand/metal mole ratios of Table J below were achieved. The mixture was stirred for 5–10 minutes before being transferred to a 100 milliliter stainless steel Parr autoclave.

The desired quantity of butadiene was then added by syringe. The bomb was then pressurized with about 25% of the desired final pressure of carbon monoxide and about 25% of the desired final hydrogen partial pressure before being heated to the final desired reaction temperature, when carbon monoxide and hydrogen were added in an amount to achieve the desired final partial pressures (all indicated in Table J). The reaction was allowed to proceed for the indicated length of time. When the total pressure had dropped to 90% of the desired total pressure, 2:1 synthesis gas (a mixture of hydrogen and carbon monoxide) was added to raise the total pressure back to 100% of that desired. The reactor was cooled to ambient temperature and vented to atmospheric pressure and the contents analyzed by gas chromatography to give the results indicated in Table K below.

L below, 3 milliliters of butadiene, 26 milliliters of solvent indicated in Table L, and 1 milliliter of digylme as internal standard. The reactor was pressurized with 5 –10 psi of 1/1 hydrogen/carbon monoxide, and heated to the desired temperature. At the desired temperature, the reactor was pressurized to the desired ratio and pressure with hydrogen and carbon monoxide, and the gas uptake was monitored. After 10% gas uptake, the reactor was re-pressurized to the initial value with 1/1 hydrogen/carbon monoxide. Samples of the reaction mixture were taken in dry ice cooled vials via the sampling line at scheduled intervals and analyzed by gas chromatography. At the end of the reaction period of 90 minutes, the gases were vented and the reaction mixture drained and stored in storage bottles under nitrogen. Further details and results are illustrated in Table L.

TABLE J

| Example | PhP($CH_2CN$)$_2$/Rh | PEt$_3$/Rh | Butadiene (mmols) | Temp (° C.) | P(CO) (psig) | P($H_2$) (psig) | Time (min) |
|---|---|---|---|---|---|---|---|
| 53 | 2 | 1 | 68.1 | 70 | 800 | 150 | 138 |
| 54 | 2 | 5 | 100.6 | 70 | 200 | 150 | 138 |
| 55 | 8 | 5 | 68.5 | 70 | 800 | 150 | 123 |
| 56 | 2 | 1 | 67.4 | 100 | 800 | 450 | 110 |
| 57 | 8 | 1 | 67.4 | 100 | 200 | 450 | 110 |
| 58 | 2 | 5 | 68.1 | 100 | 200 | 450 | 127 |
| 59 | 8 | 5 | 68.1 | 100 | 800 | 450 | 128 |
| 60 | 5 | 3 | 68.4 | 85 | 500 | 300 | 127 |

TABLE K

| Example | Penten-1-als | Penten-1-ols | 6-Hydroxy-hexanal | 1,6-Hexanediol |
|---|---|---|---|---|
| 53 | 11.0 | 74.9 | 0.0 | 0.0 |
| 54 | 5.2 | 70.8 | 0.0 | 0.0 |
| 55 | 43.4 | 47.3 | 0.0 | 0.0 |

TABLE L

| Ex. No. | Solvent/Promoter | Phosphine (Phosphine:Rh) | Temp. (° C.) | $H_2$/CO (psi) | Butadiene Conv. (%) | Rate m/L/h | 1,6-Hexanediol (%) |
|---|---|---|---|---|---|---|---|
| 61 | Diphenylamine | Trioctylphosphine (4) | 80 | 600/200 | 80 | 0.6 | 6 |
| 62 | Ethanol | Triethylphosphine (10.5) | 100 | 300/300 | 74 | 1.4 | 7 |
| 63 | Ethanol | Triethylphosphine (3.5) | 80 | 300/300 | 71 | 1.0 | 5 |
| 64 | Acetamide | Trioctylphosphine (4) | 90 | 600/200 | 84 | 0.8 | 3 |
| 65 | N-Methylacetamide | Trioctylphosphine (4) | 90 | 600/200 | 73 | 0.5 | 8 |
| 66 | Pyrrole | Trioctylpbosphine (4) | 80 | 600/200 | 90 | 1.4 | 5 |

TABLE K-continued

| Example | Penten-1-als | Penten-1-ols | 6-Hydroxy-hexanal | 1,6-Hexanediol |
|---|---|---|---|---|
| 56 | 65.1 | 3.4 | 0.0 | 0.0 |
| 57 | 71.3 | 1.4 | 0.0 | 0.0 |
| 58 | 0.5 | 69.1 | 0.9 | 6.3 |
| 59 | 5.4 | 68.8 | 2.5 | 3.5 |
| 60 | 14.9 | 49.9 | 3.4 | 1.2 |

EXAMPLES 61–66

A 100 milliliter overhead stirred high pressure reactor was charged with 0.25 mmol of dicarbonylacetylacetonato rhodium (I), 0.9–2.6 mmol of a phosphine indicated in Table

EXAMPLES 67 AND 68

A 100 milliliter overhead stirred high pressure reactor was charged with 0.25 mmol of dicarbonylacetylacetonato rhodium (I), 0.9 mmol of phosphine indicated in Table M below, 2 milliliters of the unsaturated substrate (pentenal or pentenol) indicated in Table M, 26 milliliters of solvent indicated in Table M, and 1 milliliter of digylme as internal standard. The reactor was pressurized with 100 psi of 1/1 hydrogen/carbon monoxide, and heated to the desired temperature. At the desired temperature, the reactor was pressurized to the desired pressure with 1/1 hydrogen and carbon monoxide and reaction mixture stirred for 2–4 hours. At the end of the reaction period, the gases were vented and the reaction mixture drained and analyzed by gas chromatography. Further details and results are illustrated in Table M

TABLE M

| Ex. No. | Substrate | Solvent/Promoter | Phosphine (Phosphine:Rh) | Temp. (° C.) | H₂/CO (psi) | 1,6-Hexanediol (%) |
|---|---|---|---|---|---|---|
| 67 | 4-Pentenol | Ethanol | Triethylphosphine (3.5) | 120 | 300/300 | 69 |
| 68 | 4-Pentenal | Pyrrole | Trioctylphosphine (4) | 120 | 300/300 | 59 |

EXAMPLE 69

Reactor System

The reaction system consisted of an Applied Test Systems, Inc. furnace equipped with a ⅜ inch×22 inch quartz tube reaction zone. The tube was charged in the following order with a 2 centimeter glass wool plug, 3 centimeters of 2 millimeter lead-free glass beads, 12 centimeters of Engelhard Cu-1186T ⅛ inch pelleted catalyst, and 20 centimeters of 2 milliliter lead-free glass beads. The quartz tube was placed in the furnace so as to center the catalyst inside the furnace. The tube was equipped with two thermocouples, one at the top of the catalyst bed and one at the bottom of the catalyst bed. The system was equipped with nitrogen gas and hydrogen gas metered feeds. A cold trap was used to condense product from the gas flow. The reactor ran at atmospheric pressure. The reactants were fed to the system via a syringe pump and dripped onto the glass beads to vaporize.

Catalyst Activation

A nitrogen gas flow of 51 cubic centimeters per minute was started. The furnace was heated to 230° C. Once the temperature was stabilized, a hydrogen gas flow of 5 cubic centimeters per minute was initiated. Over a two hour period the hydrogen gas flow was increased to 51cubic centimeters per minute. An exotherm associated with the catalyst reduction was observed by the top thermocouple. The catalyst activation was complete when an exotherm was observed by the bottom thermocouple and subsides. The catalyst bed temperature was raised to 260° C. A 0.012 milliliter per minute diethylene glycol feed was started and allowed to run 24 hours. The product condensate was sampled after 24 hours and analyzed via gas chromatography. The analysis showed >90% conversion and selectivity to 1,4-dioxanone from diethylene glycol. The diethylene glycol dehydrogenation was performed to determine if the catalyst was active.

1,6-Hexanediol Dehydrogenation

The reactant feed was shut off, the hydrogen feed was shut off, and the syringe pump, feed lines and product receiver were cleaned out. The syringe pump was filled with a solution of 75 grams of glyme and 50 grams of 1,6-hexanediol. The hydrogen feed was started and maintained at 51 cubic centimeters per minute. The nitrogen feed was maintained at 51 cubic centimeters per minute. The 1,6-hexanediol feed was started at 0.024 milliliters per minute. The top thermocouple temperature read 264° C. The catalyst bed temperature was maintained at about 260° C. (as measured by the top thermocouple) for the remainder of the run. The reactor was run under these conditions for 24 hours. The products and unreacted feed were condensed from the gas stream via an air cooled condenser. After 24 hours reaction time, the reactor was shut down and 5.0 grams of crude product was removed from the product collecting condenser. The crude product was analyzed via gas chromatography. The analysis of the crude product showed 13.2% glyme, 25.0% 1,6-hexandiol, 30.9% caprolactone, and several other unidentified byproducts making up the remainder of the sample. The gas chromatograph was not calibrated and the results are area% analysis. The caprolactone product was confirmed via gas chromatograph/infrared/mass spectrograph analysis.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A one step process for producing one or more substituted or unsubstituted 1,6-hexanediols which comprises subjecting one or more substituted or unsubstituted penten-1-ols comprising cis-3-penten-1-ol, trans-3-penten-1-ol, 4-penten-1-ol, cis-2-penten-1-ol and/or trans-2-penten-1-ol to reductive hydroformylation and isomerization in the presence of a reductive hydroformylation and isomerization catalyst to produce said one or more substituted or unsubstituted 1,6-hexanediols.

2. A one step process for producing one or more substituted or unsubstituted 1,6-hexanediols which comprises subjecting one or more substituted or unsubstituted pentenals comprising cis-3-pentenal, trans-3-pentenal, 4-pentenal, cis-2-pentenal and/or trans-2-pentenal to reductive hydroformylation and isomerization in the presence of a reductive hydroformylation and isomerization catalyst to produce said one or more substituted or unsubstituted 1,6-hexanediols.

3. The process of claim 1 wherein the reductive hydroformylation and isomerization catalyst comprises a metal-ligand complex catalyst.

4. The process of claim 3 wherein said metal-ligand complex catalyst comprises a metal selected from a Group 8, 9 and 10 metal complexed with an organophosphorus ligand selected from a mono-, di-, tri- and poly-(organophosphine) ligand.

5. The process of claim 3 wherein said metal-ligand complex catalyst comprises a metal selected from a Group 8, 9 and 10 metal complexed with an organophosphorus ligand selected from:

(i) a triorganophosphine ligand represented by the formula:

wherein each $R^1$ is the same or different and is a substituted or unsubstituted monovalent hydrocarbon radical;

(ii) a monoorganophosphite represented by the formula:

wherein $R^3$ represents a substituted or unsubstituted trivalent hydrocarbon radical containing from 4 to 40 carbon atoms or greater;

(iii) a diorganophosphite represented by the formula:

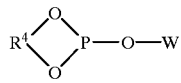

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and is a substituted or unsubstituted monovalent hydrocarbon radical; and (v) an organopolyphosphite containing two or more tertiary (trivalent) phosphorus atoms represented by the formula:

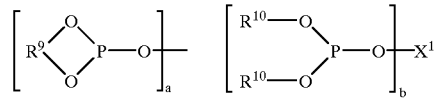

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

6. The process of claim 3 wherein said metal-ligand complex catalyst comprises a metal selected from a Group 8, 9 and 10 metal complexed with an organophosphorus ligand having the formula:

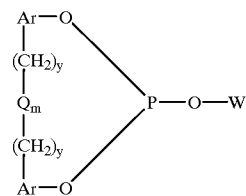

wherein W represents a substituted or unsubstituted monovalent hydrocarbon radical containing from 1 to 18 carbon atoms or greater, each Ar is the same or different and represents a substituted or unsubstituted aryl radical, each y is the same or different and is a value of 0 or 1, Q represents a divalent bridging group selected from —$C(R^5)_2$—, —O—, —S—, —$NR^6$—, $Si(R^7)_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

7. The process of claim 3 wherein said metal-ligand complex catalyst comprises a metal selected from a Group 8, 9 and 10 metal complexed with an organophosphorus ligand having the formula selected from:

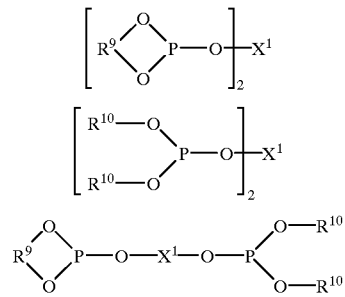

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, and each $R^{10}$ is the same or different and is a substituted or unsubstituted monovalent hydrocarbon radical containing from 1 to 24 carbon atoms.

8. The process of claim 3 wherein said metal-ligand complex catalyst comprises a metal selected from a Group 8, 9 and 10 metal complexed with an organophosphorus ligand having the formula selected from:

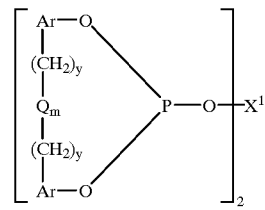

-continued

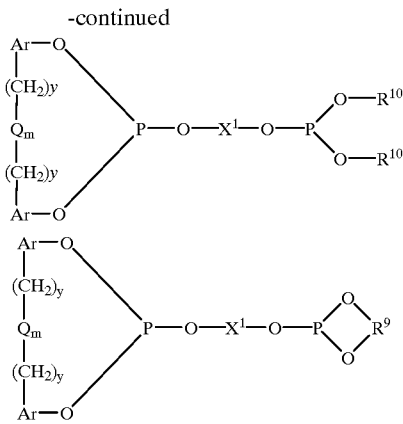

wherein X¹ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —C($R^5$)₂—, —O—, —S—, —$NR^6$—, —Si($R^7$)₂— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

9. The process of claim 1 which is conducted at a temperature from about 50° C. to 150° C. and at a total pressure from about 20 psig to about 3000 psig.

10. A one step process for producing a batchwise or continuously generated reaction mixture comprising:
    (1) one or more substituted or unsubstituted 1,6-hexanediols;
    (2) one or more substituted or unsubstituted penten-1-ols;
    (3) optionally one or more substituted or unsubstituted 6-hydroxyhexanals;
    (4) optionally one or more substituted or unsubstituted 5-hydroxypentanals and/or cyclic lactol derivatives thereof;
    (5) optionally one or more substituted or unsubstituted 4-hydroxybutanals and/or cyclic lactol derivatives thereof; and
    (6) optionally one or more substituted or unsubstituted valeraldehydes;
wherein the weight ratio of component (1) to the sum of components (3), (4), (5) and (6) is greater than about 0.1; and the weight ratio of component (2) to the sum of components (1), (3), (4), (5) and (6) is about 0 to about 100;
which process comprises subjecting one or more substituted or unsubstituted penten-1-ols comprising cis-3-penten-1-ol, trans-3-penten-1-ol, 4-penten-1-ol, cis-2-penten-1-ol and/or trans-2-penten-1-ol to reductive hydroformylation and isomerization in the presence of a reductive hydroformylation and isomerization catalyst to produce said batchwise or continuously generated reaction mixture.

11. A one step process for producing a batchwise or continuously generated reaction mixture comprising:
    (1) one or more substituted or unsubstituted 1,6-hexanediols;
    (2) one or more substituted or unsubstituted pentenals;
    (3) optionally one or more substituted or unsubstituted penten-1-ols;
    (4) optionally one or more substituted or unsubstituted 6-hydroxyhexanals;
    (5) optionally one or more substituted or unsubstituted 5-hydroxypentanals and/or cyclic lactol derivatives thereof;
    (6) optionally one or more substituted or unsubstituted 4-hydroxybutanals and/or cyclic lactol derivatives thereof;
    (7) optionally one or more substituted or unsubstituted valeraldehydes;
    (8) optionally one or more substituted or unsubstituted pentan-1-ols;
    (9) optionally one or more substituted or unsubstituted 1,6-hexanedials;
    (10) optionally one or more substituted 1,5-pentanedials; and
    (11) optionally one or more substituted 1,4-butanedials;
wherein the weight ratio of component (1) to the sum of components (3), (4), (5), (6), (7), (8), (9), (10) and (11) is greater than about 0.1; and the weight ratio of component (2) to the sum of components (1), (3), (4), (5), (6), (7), (8), (9), (10) and (11) is about 0 to about 100;
which process comprises subjecting one or more substituted or unsubstituted pentenals comprising cis-3-pentenal, trans-3-pentenal, 4-pentenal, cis-2-pentenal and/or trans-2-pentenal to reductive hydroformylation and isomerization in the presence of a reductive hydroformylation and isomerization catalyst to produce said batchwise or continuously generated reaction mixture.

12. A one step process for producing one or more substituted or unsubstituted 1,6-hexanediols which comprises subjecting one or more substituted or unsubstituted alkadienes to reductive hydroformylation in the presence of a reductive hydroformylation catalyst to produce one or more substituted or unsubstituted penten-1-ols comprising cis-3-penten-1-ol, trans-3-penten-1-ol, 4-penten-1-ol, cis-2-penten-1-ol and/or trans-2-penten-1-ol, and subjecting said one or more substituted or unsubstituted penten-1-ols to reductive hydroformylation and isomerization in the presence of a reductive hydroformylation and isomerization catalyst to produce said one or more substituted or unsubstituted 1,6-hexanediols.

13. A one step process for producing a batchwise or continuously generated reaction mixture comprising:
    (1) one or more substituted or unsubstituted 1,6-hexanediols;
    (2) optionally one or more substituted or unsubstituted penten-1-ols;
    (3) optionally one or more substituted or unsubstituted 6-hydroxyhexanals;
    (4) optionally one or more substituted or unsubstituted 5-hydroxypentanals and/or cyclic lactol derivatives thereof;
    (5) optionally one or more substituted or unsubstituted 4-hydroxybutanals and/or cyclic lactol derivatives thereof;
    (6) optionally one or more substituted or unsubstituted pentan-1-ols;
    (7) optionally one or more substituted or unsubstituted valeraldehydes;
    (8) optionally one or more substituted or unsubstituted pentenals;

(9) optionally one or more substituted or unsubstituted 1,6-hexanedials;

(10) optionally one or more substituted 1,5-pentanedials;

(11) optionally one or more substituted 1,4-butanedials; and

(12) one or more substituted or unsubstituted butadienes; wherein the weight ratio of component (1) to the sum of components (2), (3), (4), (5), (6), (7), (8), (9), (10) and (11) is greater than about 0.1; and the weight ratio of component (12) to the sum of components (1), (2), (3), (4), (5), (6), (7), (8), (9), (10) and (11) is about 0 to about 100;

which process comprises subjecting one or more substituted or unsubstituted butadienes to reductive hydroformylation in the presence of a reductive hydroformylation catalyst to produce one or more substituted or unsubstituted penten-1-ols comprising cis-3-penten-1-ol, trans-3-penten-1-ol, 4-penten-1-ol, cis-2-penten-1-ol and/or trans-2-penten-1-ol, and subjecting said one or more substituted or unsubstituted penten-1-ols to reductive hydroformylation and isomerization in the presence of a reductive hydroformylation and isomerization catalyst to produce said batchwise or continuously generated reaction mixture.

14. A one step process for producing a reaction mixture comprising one or more substituted or unsubstituted 1,6-hexanediols which process comprises subjecting one or more substituted or unsubstituted penten-1-ols comprising cis-3-penten-1-ol, trans-3-penten-1-ol, 4-penten-1-ol, cis-2-penten-1-ol and/or trans-2-penten-1-ol to reductive hydroformylation and isomerization in the presence of a reductive hydroformylation and isomerization catalyst to produce said reaction mixture comprising one or re substituted or unsubstituted 1,6-hexanediols.

15. A one step process for producing a reaction mixture comprising one or more substituted or unsubstituted 1,6-hexanediols which process comprises subjecting one or more substituted or unsubstituted pentenals comprising cis-3-pentenal, trans-3-pentenal, 4-pentenal, cis-2-pentenal and/or trans-2-pentenal to reductive hydroformylation and isomerization in the presence of a reductive hydroformylation and isomerization catalyst to produce said reaction mixture comprising one or more substituted or unsubstituted 1,6-hexanediols.

16. A one step process for producing a reaction mixture comprising one or more substituted or unsubstituted 1,6-hexanediols which process comprises subjecting one or more substituted or unsubstituted alkadienes to reductive hydroformylation in the presence of a reductive hydroformylation catalyst to produce one or more substituted or unsubstituted penten-1-ols comprising cis-3-penten-1-ol, trans-3-penten-1-ol, 4-penten-1-ol, cis-2-penten-1-ol and/or trans-2-penten-1-ol, and subjecting said one or more substituted or unsubstituted penten-1-ols to reductive hydroformylation and isomerization in the presence of a reductive hydroformylation and isomerization catalyst to produce said reaction mixture comprising one or more substituted or unsubstituted 1,6-hexanediols.

* * * * *